United States Patent
Kakimoto

(10) Patent No.: US 9,896,989 B2
(45) Date of Patent: Feb. 20, 2018

(54) DETERIORATION DIAGNOSIS DEVICE FOR OXIDATION CATALYST

(71) Applicant: NGK SPARK PLUG CO., LTD., Nagoya-shi, Aichi (JP)

(72) Inventor: Shiro Kakimoto, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 11 days.

(21) Appl. No.: 15/241,372

(22) Filed: Aug. 19, 2016

(65) Prior Publication Data

US 2016/0356199 A1 Dec. 8, 2016

Related U.S. Application Data

(62) Division of application No. 14/010,743, filed on Aug. 27, 2013, now Pat. No. 9,551,260.

(30) Foreign Application Priority Data

Aug. 30, 2012 (JP) .................................. 2012-189824
Jun. 11, 2013 (JP) .................................. 2013-122621

(51) Int. Cl.
*F01N 11/00* (2006.01)
*F01N 3/20* (2006.01)
(Continued)

(52) U.S. Cl.
CPC .............. *F01N 11/00* (2013.01); *F01N 3/035* (2013.01); *F01N 3/106* (2013.01); *F01N 3/2066* (2013.01);
(Continued)

(58) Field of Classification Search
CPC ... F01N 3/10; F01N 3/035; F01N 9/00; F01N 9/005; F01N 9/007; F01N 11/00;
(Continued)

(56) References Cited

U.S. PATENT DOCUMENTS 6,776,890 B1    8/2004  Mueller et al.
8,051,700 B2   11/2011  Wang et al.
(Continued)

FOREIGN PATENT DOCUMENTS

DE    102009000148 A1    7/2010
JP    56-150340 A    11/1981
(Continued)

OTHER PUBLICATIONS

Communication dated Oct. 13, 2016, issued by the German Patent Office in German Application No. 102013217374.1.
(Continued)

*Primary Examiner* — Mark Laurenzi
*Assistant Examiner* — Mickey France
(74) *Attorney, Agent, or Firm* — Sughrue Mion, PLLC

(57) ABSTRACT

A deterioration diagnosis device for an oxidation catalyst includes: a multi-gas sensor disposed in an exhaust passage downstream of an oxidation catalyst, the multi-gas sensor including a $NO_2$ sensor unit and a $NO_X$ sensor unit, the $NO_2$ sensor unit directly detecting a $NO_2$ concentration in exhaust gas after passing through the oxidation catalyst, and the $NO_X$ sensor unit directly detecting a $NO_X$ concentration in the exhaust gas; an NO concentration calculation unit configured to calculate an NO concentration in the exhaust gas after passing through the oxidation catalyst based on the $NO_2$ concentration and the $NO_X$ concentration; and a deterioration judgment unit configured to determine a deterioration degree of the oxidation catalyst from an evaluation value based on the NO concentration calculated by the NO concentration calculation unit.

2 Claims, 16 Drawing Sheets

(51) Int. Cl.

| | | |
|---|---|---|
| *F01N 3/035* | (2006.01) | |
| *G01N 33/00* | (2006.01) | |
| *F01N 3/10* | (2006.01) | |
| *G01N 27/414* | (2006.01) | |

(52) U.S. Cl.
CPC ....... *F01N 11/007* (2013.01); *G01N 33/0037* (2013.01); *F01N 2550/02* (2013.01); *F01N 2560/026* (2013.01); *F01N 2560/06* (2013.01); *G01N 27/414* (2013.01); *Y02T 10/24* (2013.01); *Y02T 10/47* (2013.01)

(58) Field of Classification Search
CPC ................ F01N 11/007; F01N 2550/02; F01N 2560/026; F01N 2560/02; F01N 2900/00; F01N 2900/04; F01N 2900/0412; F01N 2900/1614; G01N 33/0009; G01N 33/0037; G01N 27/407; G01N 27/416; G01N 27/417; G01N 21/3504
USPC ......... 60/272, 273, 276, 277, 282, 299, 297, 60/301; 73/114.69, 114.71, 114.75
See application file for complete search history.

(56) References Cited

U.S. PATENT DOCUMENTS

| | | |
|---|---|---|
| 8,382,973 B2 | 2/2013 | Sugaya et al. |
| 8,465,636 B2 | 6/2013 | Sugaya et al. |
| 2009/0020422 A1 | 1/2009 | A. et al. |
| 2009/0035195 A1 | 2/2009 | Robel |
| 2009/0165440 A1 | 7/2009 | Sawada et al. |
| 2009/0211906 A1 | 8/2009 | Sugaya et al. |
| 2010/0077833 A1 | 4/2010 | Wang et al. |
| 2010/0175368 A1 | 7/2010 | Schulze |
| 2010/0314264 A1 | 12/2010 | Nishijima |
| 2011/0048970 A1 | 3/2011 | Sugaya et al. |
| 2011/0120093 A1 | 5/2011 | Eckhoff et al. |
| 2011/0170102 A1 | 7/2011 | Janssen et al. |
| 2012/0233986 A1 | 9/2012 | Geveci et al. |
| 2013/0062203 A1 | 3/2013 | Nakano et al. |
| 2013/0233728 A1 | 9/2013 | Day et al. |

FOREIGN PATENT DOCUMENTS

| | | |
|---|---|---|
| JP | 6-50936 A | 2/1994 |
| JP | 11-132995 A | 5/1999 |
| JP | 11-142369 A | 5/1999 |
| JP | 2010-156243 A | 7/2010 |
| JP | 2012-36860 A | 2/2012 |
| WO | 0123730 A2 | 4/2001 |
| WO | 2010/010978 A1 | 1/2010 |

OTHER PUBLICATIONS

Communication dated Nov. 4, 2015, from the Japanese Patent Office in application No. 2013-122621.
Communication, dated Jun. 6, 2016, from the Japanese Patent Office in Japanese application No. 2013-122621.
429077 A, RD, Jan. 10, 2000, Hoving (anonymous).

DETERIORATION DIAGNOSIS DEVICE FOR OXIDATION CATALYST

CROSS-REFERENCE TO RELATED APPLICATIONS

This is a Divisional of U.S. application Ser. No. 14/010,743, filed Aug. 27, 2013, which claims priority from Japanese Application Nos. 2012-189824 and 2013-122621, filed Aug. 30, 2012 and Jun. 11, 2013, respectively. The entire disclosures of the prior applications are considered part of the disclosure of the accompanying continuation application and are hereby incorporated by reference in their entirety.

BACKGROUND OF THE INVENTION

1. Field of the Invention

The present invention relates to a device that diagnoses the deterioration of oxidation catalyst used for an exhaust gas purifier of an internal combustion engine.

2. Description of the Related Art

Recently, emissions regulation of diesel engines has been tightened. Accordingly, removing Particulate Matter (hereinafter also referred to as "PM") from exhaust air is desired by trapping PM included in the exhaust air from a diesel engine and burning the trapped PM. In this regard, an engine includes a particulate filter (a Diesel Particulate Filter, hereinafter also referred to as "DPF") to trap the PM at its exhaust passage. The DPF is made of a material such as ceramic and stainless steel. To trap the PM, the DPF includes, for example, a honeycomb structure. If the PM is excessively trapped, the DPF becomes clogged. Therefore, as one method, the DPF includes an oxidation catalyst (Diesel Oxidation Catalyst, hereinafter also referred to as "DOC") at an upstream location. The DOC oxidizes NO in the exhaust air to $NO_2$ using an oxidation catalyst. Use of the $NO_2$ thus generated allows the DOC to also oxidize and burn the PM trapped by the DPF. Thus, the PM is removed to continuously regenerate the DPF.

The performance of the DOC to generate $NO_2$ deteriorates over time due to usage. Accordingly, the regeneration performance of the DPF is also deteriorated. Therefore, a device that diagnoses the deterioration degree of the DOC has been developed (see JP-A-2012-36860).

First, this diagnosis device estimates a $NO_X$ value in the exhaust air immediately after being discharged from the engine based on engine revolution and an engine load. Also, the $NO_X$ value at the downstream side of the DOC is directly detected by a $NO_X$ sensor installed at the downstream of the DOC. Next, a $NO_2$ ratio is calculated using these two $NO_X$ values. The concentration of $NO_2$ that has passed through the DPF is obtained from the $NO_2$ ratio. The deterioration degree of the DOC is determined from this $NO_2$ concentration.

SUMMARY OF THE INVENTION

A diagnosis device which determines a deterioration degree of a DOC based on a $NO_X$ ratio calculated using two $NO_X$ values has a low diagnosis accuracy. Especially, when estimating a $NO_X$ value in exhaust air immediately after being discharged from an engine, factors other than an engine revolution and an engine load are not taken into consideration. In view of the above, depending on usage conditions, it may be the case that the estimation accuracy is significantly lowered.

It is therefore an object of the present invention to provide a deterioration diagnosis device for an oxidation catalyst that can determine the degree of deterioration of an oxidation catalyst with good accuracy, and which is disposed at an exhaust passage of an internal combustion engine to oxidize NO to $NO_2$.

The above object of the present invention has been achieved by providing (1) a deterioration diagnosis device for determining a deterioration degree of an oxidation catalyst disposed at an exhaust passage of an internal combustion engine, the deterioration diagnosis device comprising: a multi-gas sensor disposed downstream of the oxidation catalyst, the multi-gas sensor including a multi-gas sensor element unit that integrally includes a $NO_2$ sensor unit and a $NO_X$ sensor unit, the $NO_2$ sensor unit directly detecting a $NO_2$ concentration in exhaust gas after passing through the oxidation catalyst, and the $NO_X$ sensor unit directly detecting a $NO_X$ concentration in the exhaust gas; an NO concentration calculation unit configured to calculate an NO concentration in the exhaust gas after passing through the oxidation catalyst based on the $NO_2$ concentration and the $NO_X$ concentration; and a deterioration judgment unit configured to determine a deterioration degree of the oxidation catalyst from an evaluation value based on the NO concentration calculated by the NO concentration calculation unit.

Using this deterioration diagnosis device for determining a deterioration degree of an oxidation catalyst, the actual $NO_2$ concentration and the actual $NO_X$ concentration downstream of the oxidation catalyst are directly obtained from the exhaust gas using a multi-gas sensor. Based on the $NO_2$ concentration and the $NO_X$ concentration, the NO concentration is calculated. The degree of deterioration of the oxidation catalyst is diagnosed from an evaluation value based on the NO concentration. Consequently, the diagnosis can be performed with good accuracy.

The evaluation value is a value that need only by based on the NO concentration. The evaluation value may be, for example, a ratio between the NO concentration and the $NO_2$ concentration, a ratio between the NO concentration and the $NO_X$ concentration, or the NO concentration alone.

In a preferred embodiment (2) of the above deterioration diagnosis device (1), the multi-gas sensor is disposed downstream of and immediately after the oxidation catalyst.

Thus, disposing the multi-gas sensor immediately after the oxidation catalyst allows for directly measuring the exhaust gas that has passed through the oxidation catalyst at the multi-gas sensor. Consequently, the degree of deterioration of the oxidation catalyst can be diagnosed with good accuracy.

"The multi-gas sensor is disposed downstream of and immediately after the oxidation catalyst" means that the multi-gas sensor is disposed at the downstream side of the oxidation catalyst in the exhaust passage without an intermediate member interposed within the exhaust passage between the oxidation catalyst and the multi-gas sensor.

In another preferred embodiment (3), the above deterioration diagnosis device (1) further comprises a filter disposed in the exhaust passage downstream of the oxidation catalyst, the filter trapping particulate matter, wherein the multi-gas sensor is disposed downstream and immediately after the filter.

In case of disposing the multi-gas sensor immediately after the oxidation catalyst, the PM that has passed through the oxidation catalyst accumulates in the multi-gas sensor element unit. In this case, since the sensor output fluctuates, there is a concern that the sensor output cannot be obtained from the multi-gas sensor with good accuracy. In contrast, disposing the multi-gas sensor downstream and immediately after the filter can inhibit PM from accumulating in the multi-gas sensor element unit. Consequently, the degree of deterioration of the oxidation catalyst can be diagnosed with good accuracy while reducing fluctuation of the sensor output.

"The multi-gas sensor is disposed downstream and immediately after the filter" means that the multi-gas sensor is disposed downstream of the filter in the exhaust passage without an intermediate member within the exhaust passage interposed between the filter and the multi-gas sensor.

In yet another preferred embodiment (4) of the above deterioration diagnosis device of any of (1) to (3) above, the multi-gas sensor element unit includes a plurality of $NO_2$ sensor units, and the respective $NO_2$ sensor units have different sensitivity ratios relative to $NO_2$.

Using this deterioration diagnosis device for determining a deterioration degree of an oxidation catalyst, correction calculation can be precisely performed on $NO_2$ even in an environment where various inflammable gases coexist and the oxygen concentration is subject to change. Such calculation together with the $NO_X$ sensor output allows for separately detecting $NO_2$ and NO.

In yet another preferred embodiment (5) of the deterioration device of any of (1) to (4) above, the multi-gas sensor element unit has a plate shape extending in an axial direction, the multi-gas sensor element unit includes a temperature detector for controlling a temperature of the $NO_X$ sensor unit, and respective ones of the plurality of $NO_2$ sensor units at least partially overlap the temperature detector in the axial direction.

Using this deterioration diagnosis device for determining a deterioration degree of an oxidation catalyst, the temperature of the multi-gas sensor element unit can be controlled based on the temperature measured at the temperature detector. In view of the above, the temperature of the multi-gas sensor element unit is kept at the most stable value adjacent the temperature detector. Accordingly, the temperature of the $NO_2$ sensor unit is kept constant within a predetermined range by at least partially overlapping the $NO_2$ sensor unit and the temperature detector in the axial direction. Consequently, the measurement accuracy of $NO_2$ is improved.

In yet another preferred embodiment (6) of the deterioration diagnosis device of any of (1) to (5) above, the $NO_2$ sensor unit includes a solid electrolyte body having oxygen ion conductivity (at an activation temperature), a detection electrode and a reference electrode each disposed at a surface of the solid electrolyte body, and an interlayer disposed between the detection electrode and the solid electrolyte body. The interlayer contains a solid electrolyte component having oxygen ion conductivity of equal to or more than 50% by mass, the interlayer also including a first metal oxide of at least one kind of metal oxide selected from the group consisting of metal oxides of Co, Mn, Cu, Ni and Ce. Further, the detection electrode contains Au in an amount equal to or more than 70% by mass, the detection electrode not including the first metal oxide.

Using this deterioration diagnosis device for determining a deterioration degree of an oxidation catalyst, the $NO_2$ concentration can be measured at good accuracy by the $NO_2$ sensor unit with the above-described configuration. In view of above, the diagnosis accuracy of the deterioration degree of the oxygen catalyst is further improved.

DETAILED DESCRIPTION OF THE PREFERRED EMBODIMENT

In the following detailed description, for purpose of explanation, numerous specific details are set forth in order to provide a thorough understanding of the disclosed embodiments. It will be apparent, however, that one or more embodiments may be practiced without these specific details and that the present invention should not be construed as being limited thereto. In other instances, well-known structures and devices are schematically shown in order to simplify the drawings.

An embodiment of the invention will next be described in detail with reference to the drawings. Furthermore, using the deterioration diagnosis device for determining a deterioration degree of an oxidation catalyst according to the embodiment, the degree of the deterioration of the oxidation catalyst, which oxidizes NO to $NO_2$, can be diagnosed with good accuracy.

Figure 1:
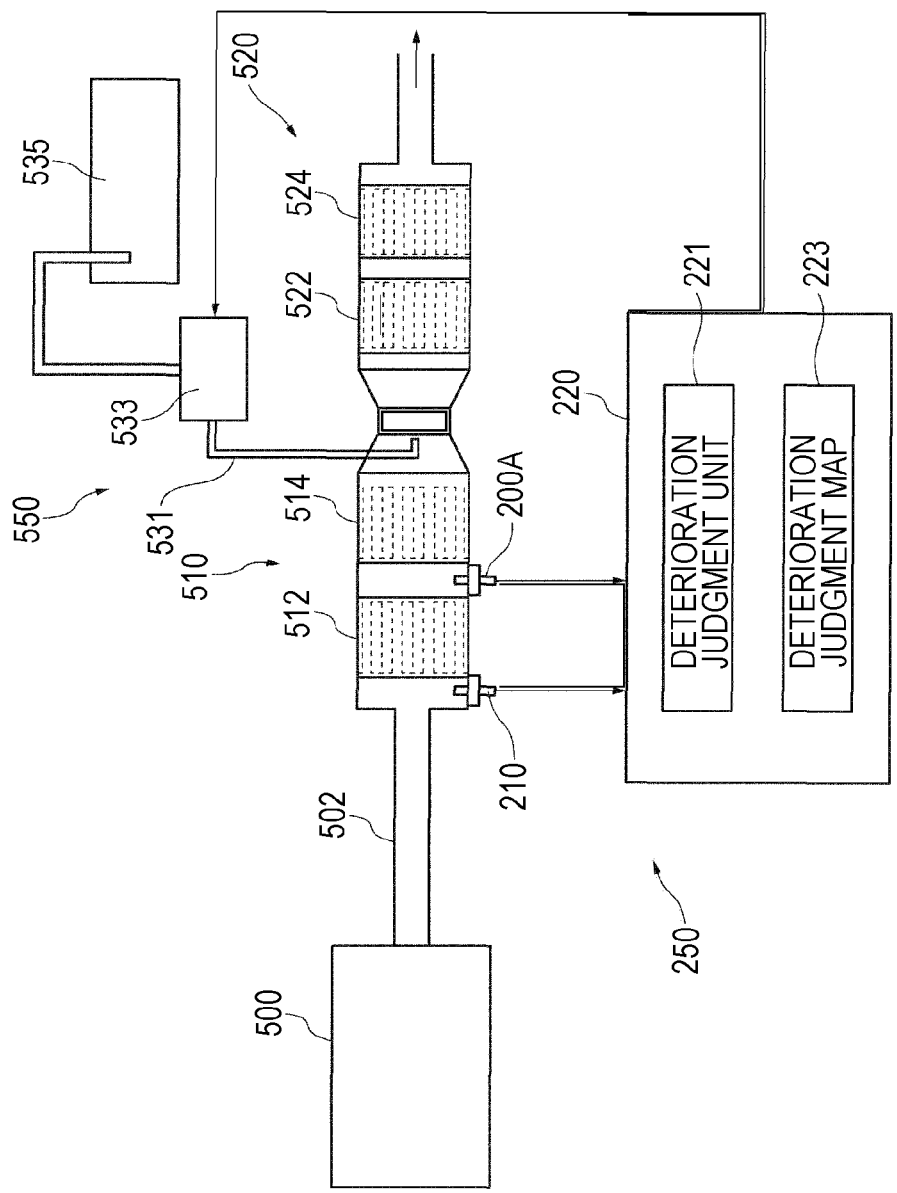
FIG. 1 is a block diagram illustrating a deterioration diagnosis device for an oxidation catalyst according to an embodiment of the invention.

FIG. 1 is a block diagram illustrating a deterioration diagnosis device for determining a deterioration degree of an oxidation catalyst 250 according to the embodiment mounted to a vehicle.

An exhaust gas purifier 550 is mounted in the middle of an exhaust pipe (an exhaust passage) 502 of an engine (a diesel engine) 500, which is an internal combustion engine of the vehicle. The exhaust gas purifier 550 purifies an exhaust gas discharged from the engine 500. The exhaust gas purifier 550 includes an upstream side exhaust gas purifier (also referred to as a "DPF device") 510 and a downstream side exhaust gas purifier (also referred to as a "SCR device") 520 disposed in this order from the upstream side of the exhaust pipe 502. The exhaust gas purifier 550 further includes a urea water addition nozzle 531 disposed between the DPF device 510 and the SCR device 520.

The deterioration diagnosis device 250 includes a multi-gas sensor 200A and a temperature sensor 210, which are mounted to the DPF device 510, and a controller (ECU, Engine (electronic) Control Unit) 220. The ECU 220 diagnoses a deterioration degree of an oxidation catalyst (DOC) 512, described below, based on the detected outputs of the multi-gas sensor 200A and the temperature sensor 210.

The DPF device 510 includes a tubular casing. This tubular casing internally includes the oxidation catalyst (Diesel Oxidation Catalyst, hereinafter referred to as "DOC") 512 and a particulate filter (Diesel Particulate Filter, hereinafter referred to as "DPF") 514 in this order from the upstream side. The DPF 514 includes, for example, a porous filter (for example, a ceramic filter) that traps Particulate Matter (PM). The DOC 512 includes a honeycomb-shaped carrier made of, for example, metal or ceramic. This carrier supports a catalytic material that oxidizes NO to $NO_2$. The DOC 512 oxidizes NO in the exhaust gas to $NO_2$. Use of this $NO_2$ allows the DOC 512 to oxidize and burn PM trapped in the DPF 514, thus removing the PM. This allows continuous regeneration of the DPF 514. The regeneration of the DPF 514 is controlled by the ECU 220.

The SCR device 520 has a tubular casing. This tubular casing internally includes a Selective Catalytic Reduction (hereinafter referred to as "SCR") 522 and a latter part oxidation catalyst (Clean Up Catalyst, hereinafter abbreviated as CUC) 524 in this order from the upstream side. The SCR 520 is a catalyst that reduces $NO_X$ in the exhaust gas to $N_2$ using ammonia supplied from the upstream as a reducing agent. The SCR 520, for example, may be a zeolitic catalyst or a vanadium catalyst. The CUC 524 is an oxidation catalyst that removes ammonia that has not reacted at the SCR 522.

The urea water addition nozzle 531 injects urea water from a urea water tank 535 into the exhaust gas at the upstream side of the SCR 522 by an addition device 533. The urea water injected upstream of the SCR 522 into the exhaust gas is hydrolyzed, thus generating ammonia. This ammonia acts as a reducing agent in the SCR 522. The addition of the urea water is controlled by the ECU 220.

The ECU 220 calculates NO concentration in the exhaust gas that has passed through the DOC 512. The ECU 220 further includes a deterioration judgment unit 221. The deterioration judgment unit 221 determines the deterioration degree of the DOC 512 using a predetermined model (a deterioration judgment map 223 or a calculating formula).

The ECU 220 also performs various controls of the engine, the regeneration control of the above-described DPF 514, and the addition control of the urea water.

The ECU 220 is an electronic control unit (ECU) that includes a microcomputer including a central processing unit (CPU), RAM, ROM, and similar member, and a predetermined analog circuit. In the ECU 220, the CPU executes a computer program stored in the ROM. This allows performing various processes described below.

Specifically, the deterioration judgment unit 221 is implemented as a CPU that executes the computer program stored in the ROM. The deterioration judgment map 223 is stored in a storage medium disposed separately from the microcomputer.

The DPF device 510 internally includes the temperature sensor 210 at the upstream side of the DOC 512. The multi-gas sensor 200A is installed at the downstream side immediately after the DOC 512. Thus, the multi-gas sensor 200A is disposed immediately after the oxidation catalyst. This allows the multi-gas sensor 200A to directly measure the exhaust gas that has passed through the oxidation catalyst. As a result, the degree of deterioration of the oxidation catalyst can be diagnosed with good accuracy. The temperature sensor 210 detects the temperature of the exhaust gas that has flowed into the DOC 512. This exhaust gas temperature is taken as the catalyst temperature of the DOC 512.

In the details illustrated in FIG. 4 to FIG. 6, described below, the multi-gas sensor 200A includes a $NO_2$ sensor unit 42 and a $NO_X$ sensor unit 30A. The $NO_2$ sensor unit 42 and the $NO_X$ sensor unit 30A directly detect the $NO_2$ concentration and the $NO_X$ concentration in the exhaust gas that has passed through the DOC 512, respectively. A control device 300 is connected to the multi-gas sensor 200A. The control device 300 can calculate NO concentration=($NO_X$ concentration−$NO_2$ concentration) using the detected $NO_2$ concentration and the detected $NO_X$ concentration. This NO concentration is a value calculated using the measured values of the $NO_2$ concentration and the $NO_X$ concentration in the exhaust air. Thus, the NO concentration determined in accordance with this invention expresses an actual NO concentration that is different from the estimated value disclosed in the above-described JP-A-2012-36860.

Figure 2:
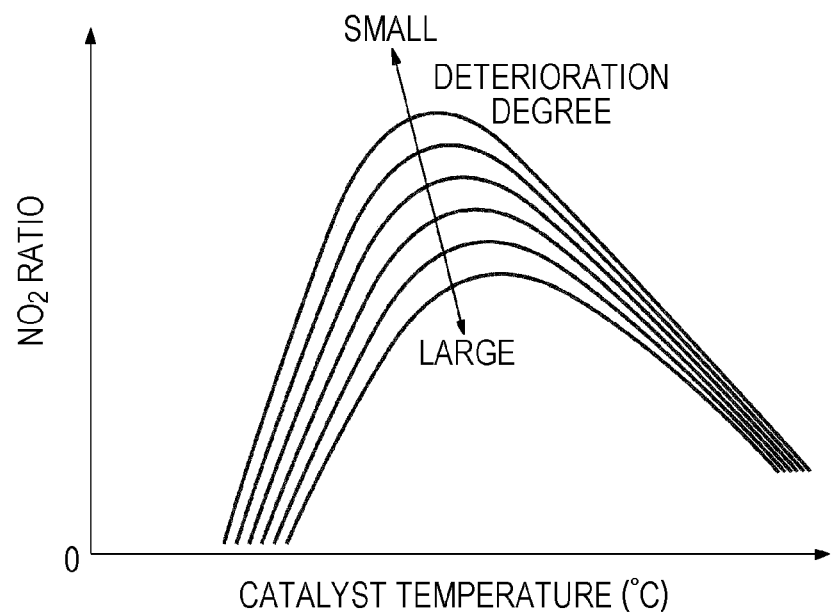
FIG. 2 is a diagram illustrating a map that is used to determine a deterioration degree of the oxidation catalyst.

The deterioration judgment map 223 is illustrated in FIG. 2. The deterioration degree of the DOC 512 relates to the catalyst temperature of the DOC 512 and $NO_2$ ratio ($NO_2$ concentration/NO concentration). At the same catalyst temperature, the smaller the $NO_2$ ratio (that is, when the $NO_2$ generation amount is small), the larger the deterioration degree. Accordingly, the deterioration degree of the DOC 512 can be judged as follows. The $NO_2$ ratio is calculated based on the $NO_2$ concentration detected by the multi-gas sensor 200A and the NO concentration calculated by the control device 300. Then, the deterioration judgment map 223 is referred to using this $NO_2$ ratio and the temperature detected by the temperature sensor 210.

Figure 3:
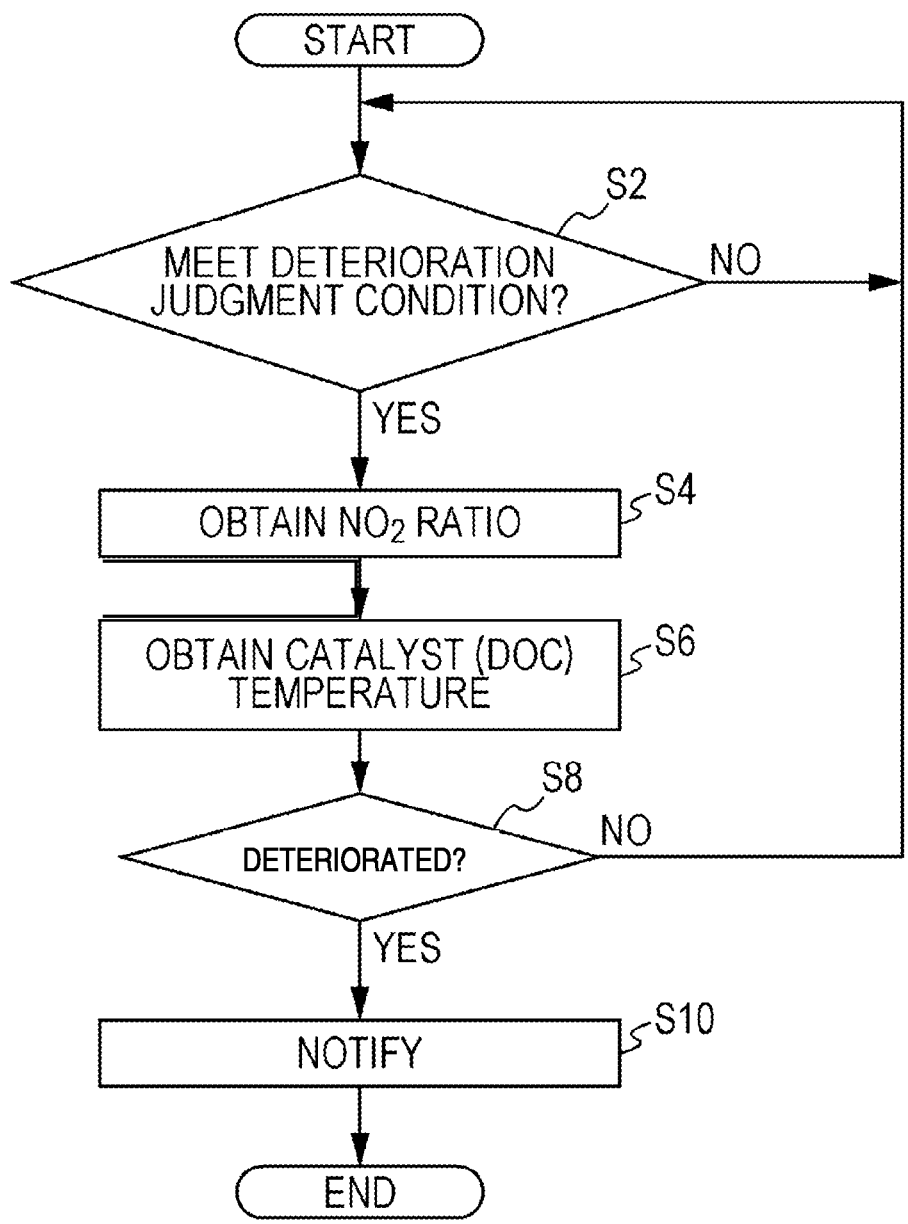
FIG. 3 is a flowchart illustrating a process performed by the deterioration diagnosis device for an oxidation catalyst.

FIG. 3 is a flowchart for a deterioration determination processing flow performed by the deterioration judgment unit 221. First, the deterioration judgment unit 221 determines whether or not a deterioration judgment condition is met (Step S2). A "Yes" determination is made in Step S2 when, for example, the temperature detected by the temperature sensor 210 is within a predetermined range, and the process progresses to Step S4. If a "No" determination is made in Step S2, the process returns. In Step S4, the deterioration judgment unit 221 obtains the $NO_2$ ratio ($NO_2$ concentration/NO concentration) from the control device 300, described below. In Step S6, the deterioration judgment unit 221 obtains the value of the catalyst temperature from the temperature sensor 210. Next, in Step S8, the deterioration judgment unit 221 refers to the deterioration judgment map 223 using the $NO_2$ ratio and the catalyst temperature, and determines the deterioration degree of the DOC 512. If a "Yes" determination is made in Step S8 (if the DOC 512 is determined to be deteriorated), the deterioration judgment unit 221 notifies a driver of a vehicle or similar person of the deterioration of the DOC 512 using, for example, a predetermined buzzer or an indicator, and then the process is terminated (Step S10). If a "No" determination is made in Step S8, the process returns to the first process in the processing flow.

As described above, in this embodiment, the $NO_2$ ratio is calculated using the actual $NO_2$ concentration and the actual NO concentration. In view of the above, the degree of the deterioration of the oxidation catalyst can be determined with good accuracy. In Step S8, the deterioration degree is determined from the map where the deterioration of the oxidation catalyst is correlated using the $NO_2$ ratio and the catalyst temperature. In Step S8, the deterioration degree may be determined from the map where the deterioration of the oxidation catalyst is correlated using the absolute value of the NO concentration and the catalyst temperature instead of using the $NO_2$ ratio.

The $NO_2$ ratio is calculated by the control device 300. The control device 300 calculates the NO concentration by NO concentration=($NO_X$ concentration–$NO_2$ concentration) using the $NO_2$ concentration and the $NO_X$ concentration directly detected at the $NO_2$ sensor unit 42 and the $NO_X$ sensor unit 30A.

Figure 4:
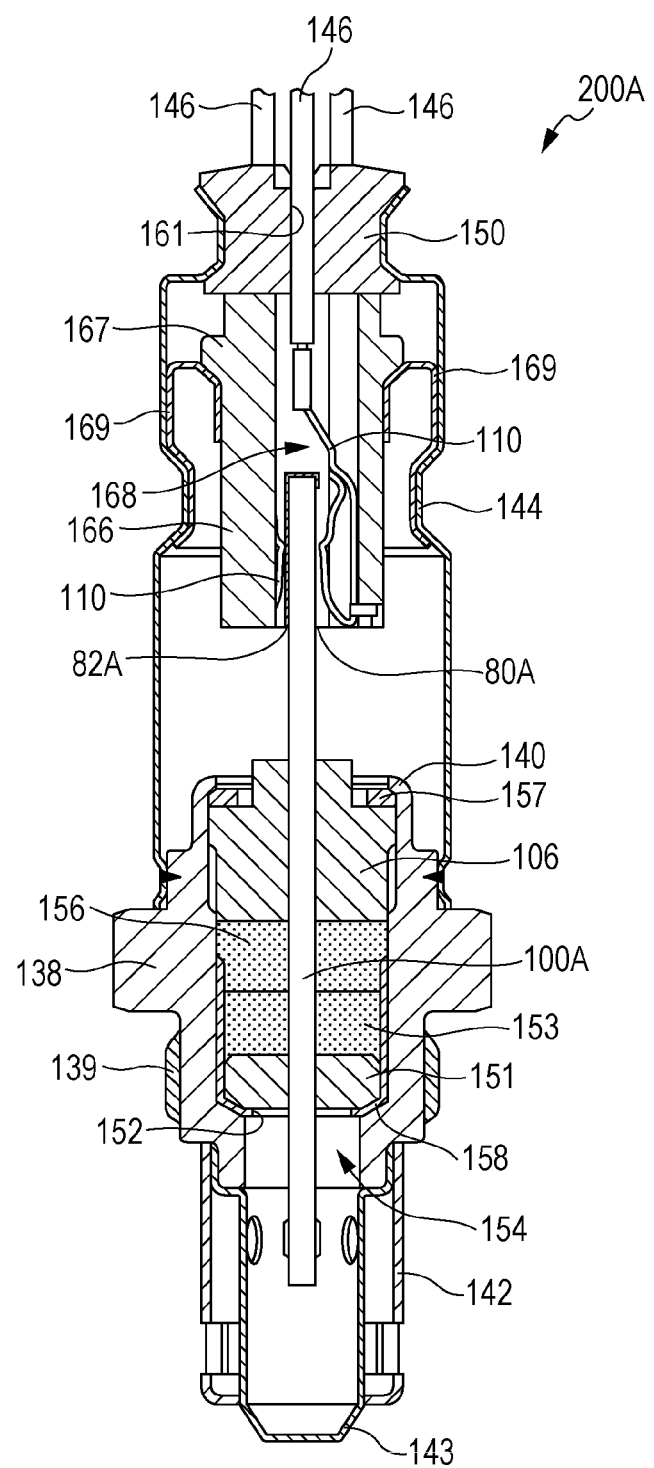
FIG. 4 is a sectional view of a multi-gas sensor along a longitudinal direction.

FIG. 4 is a sectional view of the multi-gas sensor 200A along a longitudinal direction. The multi-gas sensor 200A is an assembly where a multi-gas sensor element unit 100A is assembled. The multi-gas sensor element unit 100A detects the $NO_2$ concentration and the $NO_X$ concentration. The multi-gas sensor 200A includes the plate-shaped multi-gas sensor element unit 100A extending in an axial direction, a tubular metal shell 138, a tubular ceramic sleeve 106, an insulating contact member 166, and a plurality of (in FIG. 3, only two terminal are illustrated) connection terminal 110. The tubular metal shell 138 includes a thread portion 139 to secure the multi-gas sensor 200A to the exhaust pipe at the outer surface. The tubular ceramic sleeve 106 is disposed so as to surround the peripheral area of the multi-gas sensor element unit 100A in the radial direction. The insulating contact member 166 is disposed so that the inner wall surface of a contact insertion hole 168 penetrating in the axial direction surrounds the peripheral area of the rear end portion of the multi-gas sensor element unit 100A. The connection terminal 110 are disposed between the multi-gas sensor element unit 100A and the insulating contact member 166.

The metal shell 138 has an approximately tubular shape. The metal shell 138 includes a penetration pin hole 154 and a shoulder portion 152. The penetration pin hole 154 penetrates in the axial direction. The shoulder portion 152 projects in the radially inward direction of the penetration pin hole 154. The metal shell 138 holds the multi-gas sensor element unit 100A in the penetration pin hole 154 while the front end side of the multi-gas sensor element unit 100A is disposed at the outside of the front end side of the penetration pin hole 154. Also, electrode terminal portions 80A and 82A are disposed at the outside of the rear end side of the penetration pin hole 154. The shoulder portion 152 includes an inward tapered surface inclined with respect to a planar surface vertical to the axial direction.

In the penetration pin hole 154 of the metal shell 138, a ring-shaped ceramic holder 151, powder filled layers 153 and 156 (hereinafter also referred to as talc rings 153 and 156), and the above-described ceramic sleeve 106 are laminated in this order from the front end side to the rear end side. The ring-shaped ceramic holder 151, the powder filled layers 153 and 156, and the ceramic sleeve 106 surround the peripheral area of the multi-gas sensor element unit 100A in the radial direction. A crimp packing 157 is disposed between the ceramic sleeve 106 and a rear end portion 140 of the metal shell 138. For maintaining air tightness, a metal holder 158 is disposed between the ceramic holder 151 and the shoulder portion 152 of the metal shell 138. The metal holder 158 holds the talc ring 153 or the ceramic holder 151. The rear end portion 140 of the metal shell 138 is crimped so that the ceramic sleeve 106 is pressed to the front end side of the metal shell 138 via the crimp packing 157.

Meanwhile, as illustrated in FIG. 4, double protectors (an outer protector 142 and an inner protector 143), which are made of metal (for example, stainless steel), are installed to the outer periphery of the front end side (the lower side in FIG. 4) of the metal shell 138 by, for example, welding. The outer protector 142 and the inner protector 143 cover the projection portion of the multi-gas sensor element unit 100A and include a plurality of hole portions.

A shell 144 is secured to the outer periphery of the rear end side of the metal shell 138. A grommet 150 is disposed at the opening of the rear end side (the upper side in FIG. 4) of the shell 144. The grommet 150 includes a lead wire insertion hole 161. A plurality of lead wires 146 (only three wires are illustrated in FIG. 4) is inserted through the lead wire insertion hole 161. The respective plurality of lead wires 146 are electrically connected to the electrode terminal portions 80A and 82A of the multi-gas sensor element unit 100A. For simplification, in FIG. 4, only the electrode terminal portions 80A and 82A are illustrated as electrode terminal portions of the front face and the reverse face of the multi-gas sensor element unit 100A. In practice, a plurality of the electrode terminal portions is formed according to the number of electrodes of the $NO_X$ sensor unit 30A and the $NO_2$ sensor unit 42, described below, or the number of similar members.

The metal shell 138 includes the insulating contact member 166 at the rear end side (the upper side in FIG. 4) of the multi-gas sensor element unit 100A projecting from the rear end portion 140. This insulating contact member 166 is disposed at the peripheral area of the electrode terminal portions 80A and 82A, which are formed at the front and the reverse faces at the rear end side of the multi-gas sensor element unit 100A. This insulating contact member 166 has a tubular shape. The insulating contact member 166 includes the contact insertion hole 168 penetrating in the axial direction. This insulating contact member 166 includes a flange portion 167 projecting from the outer surface in the radially outward direction. The flange portion 167 abuts the shell 144 via a supporting member 169. Accordingly, the insulating contact member 166 is disposed inside of the shell 144. The connection terminal 110 at the insulating contact member 166 side electrically connects to the electrode terminal portions 80A and 82A of the multi-gas sensor element unit 100A. The connection terminal 110 is in a continuity state with the outside through the lead wire 146.

Figure 5:
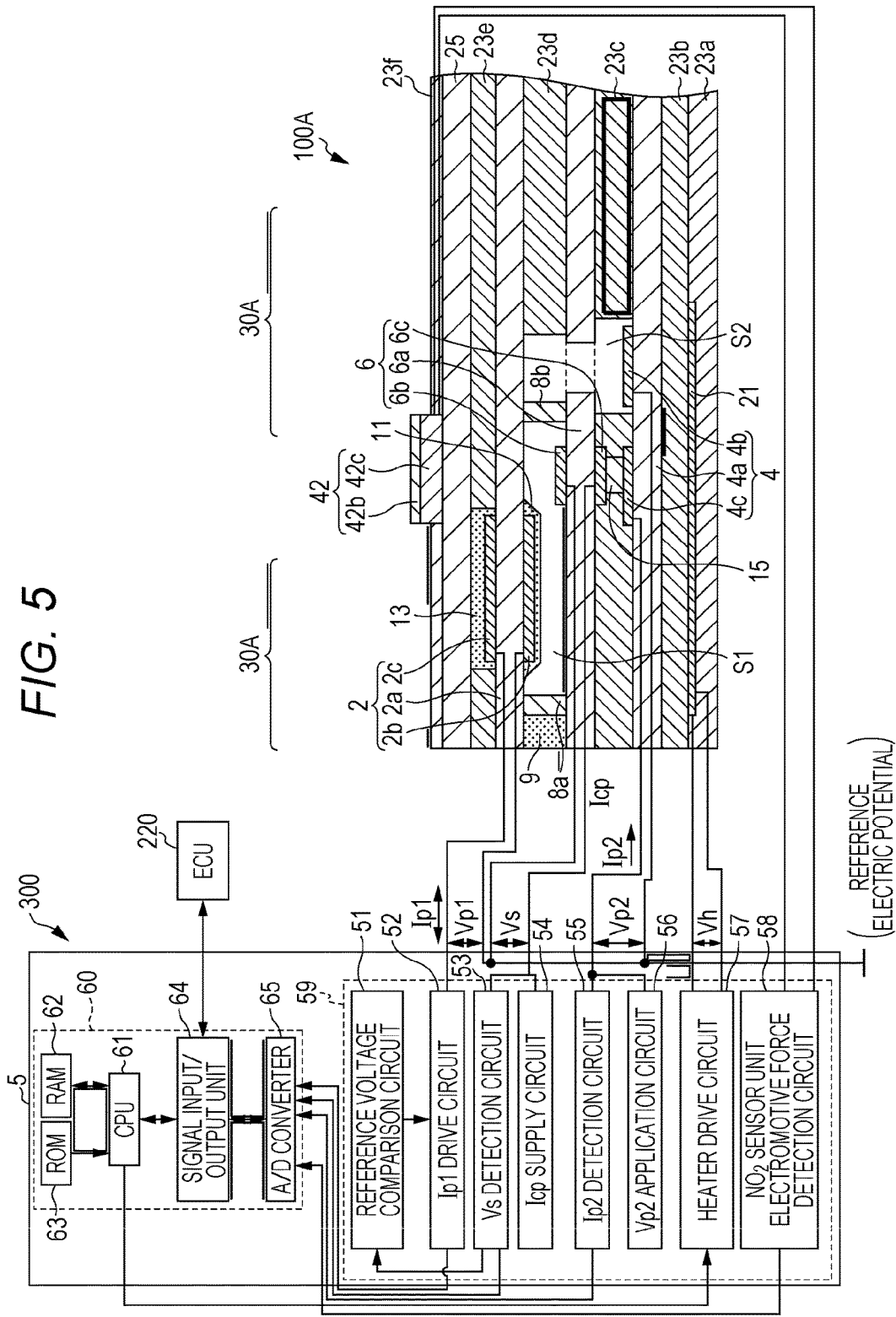
FIG. 5 is a block diagram illustrating a configuration of the multi-gas sensor and a gas sensor control device.

FIG. 5 is a block diagram illustrating configurations of the control device (controller) 300 and the multi-gas sensor element unit 100A, which is connected to the control device 300, according to the embodiment. In FIG. 5, a cross section of the multi-gas sensor element unit 100A housed in the multi-gas sensor 200A along the longitudinal direction is illustrated for convenience of explanation.

The multi-gas sensor 200A (the multi-gas sensor element unit 100A) and the control device 300 are mounted to the vehicle with an internal combustion engine (an engine) (not shown). The control device 300 is electrically connected to the ECU 220. The end of the lead wire 146 extending from the multi-gas sensor 200A is connected to the connector. This connector is electrically connected to the connector on the control device 300 side.

Next, the configuration of the multi-gas sensor element unit 100A will be described. The multi-gas sensor element unit 100A includes the $NO_X$ sensor unit 30A and the $NO_2$ sensor unit 42. The $NO_X$ sensor unit 30A may include a similar configuration as known $NO_X$ sensors. In the detailed description below, the $NO_2$ sensor unit 42 is formed at the outer surface of the $NO_X$ sensor unit 30A.

The $NO_X$ sensor unit 30A is constructed by laminating an insulation layer 23f, a solid electrolyte body for $NO_2$ sensor 25, an insulation layer 23e, a first solid electrolyte body 2a, an insulation layer 23d, a third solid electrolyte body 6a, an insulation layer 23c, a second solid electrolyte body 4a, and insulation layers 23b and 23a in this order. A first measuring chamber S1 is defined between the layers of the first solid electrolyte body 2a and the third solid electrolyte body 6a. Exhaust gas is introduced from the outside via a first diffusion resistive element 8a disposed at the left end (the inlet) of the first measuring chamber S1. A protective layer 9 including a porous material is disposed outside of the first diffusion resistive element 8a.

A second diffusion resistive element 8b is disposed at the end opposite the inlet of the first measuring chamber S1. A second measuring chamber (corresponding to the "$NO_X$ measuring chamber" of the invention) S2 is defined at the right side of the first measuring chamber S1. The second measuring chamber S2 communicates with the first measuring chamber S1 via the second diffusion resistive element 8b. The second measuring chamber S2 penetrates the third solid electrolyte body 6a. The second measuring chamber S2 is formed between the layers of the first solid electrolyte body 2a and the second solid electrolyte body 4a.

An elongated plate-shaped heater 21 is buried between the insulation layers 23b and 23a. The heater 21 extends along the longitudinal direction of the multi-gas sensor element unit 100A. The heater 21 stabilizes operation of the $NO_X$ sensor unit 30A. That is, the heater 21 raises the temperature of the $NO_X$ sensor unit 30A to its activation temperature and enhances oxygen ion conductivity of the solid electrolyte body. The chief material forming each of the insulation layers 23a, 23b, 23c, 23d, 23e and 23f is alumina. The first diffusion resistive element 8a and the second diffusion resistive element 8b include a porous material such as alumina. The heater 21 includes, for example, platinum.

A first pumping cell 2 includes the first solid electrolyte body 2a, an inner first pumping electrode 2b, and an outer first pumping electrode 2c. The first solid electrolyte body 2a includes zirconia having oxygen ion conductivity as the chief material. The inner first pumping electrode 2b and the outer first pumping electrode 2c, which is disposed opposite the inner first pumping electrode 2b, sandwich the first solid electrolyte body 2a. The inner first pumping electrode 2b faces the first measuring chamber S1. The chief material forming both the inner first pumping electrode 2b and the outer first pumping electrode 2c is platinum. The surface of the inner first pumping electrode 2b is covered with a protective layer 11 including a porous body.

The insulation layer 23e, which is equivalent to the top surface of the outer first pumping electrode 2c, is partially hollowed out. A porous body 13 fills the hollowed portion. This allows communication between the outer first pumping electrode 2c and the outside to allow for entrance and exit of gas (oxygen).

An oxygen concentration detection cell 6 includes the third solid electrolyte body 6a, a detection electrode 6b, and a reference electrode 6c. The third solid electrolyte body 6a is formed from zirconia as a chief material. The detection electrode 6b and the reference electrode 6c sandwich the third solid electrolyte body 6a. The detection electrode 6b is disposed downstream of the inner first pumping electrode 2b and faces the first measuring chamber S1. The chief material forming both the detection electrode 6b and the reference electrode 6c is platinum.

The insulation layer 23c is cut out so that the reference electrode 6c in contact with the third solid electrolyte body 6a is internally disposed therein. A porous body fills the cutout portion. Thus, a reference oxygen chamber 15 is formed. A weak current is preliminarily passed through the oxygen concentration detection cell 6 at a constant value using an Icp supply circuit 54. This transports oxygen from the first measuring chamber S1 to the inside of the reference oxygen chamber 15. The reference electrode 6c is thereby exposed to a predetermined oxygen concentration, which serves as a reference.

A second pumping cell 4 includes the second solid electrolyte body 4a, an inner second pumping electrode 4b, and a counterpart second pumping electrode 4c. The second solid electrolyte body 4a is formed from zirconia as a chief material. The inner second pumping electrode 4b is disposed on the surface facing the second measuring chamber S2 of the second solid electrolyte body 4a. The counterpart second pumping electrode 4c forms a counterpart electrode of the inner second pumping electrode 4b. The chief material forming both the inner second pumping electrode 4b and the counterpart second pumping electrode 4c is platinum.

The counterpart second pumping electrode 4c is disposed at the cutout portion of the insulation layer 23c on the second solid electrolyte body 4a. The counterpart second pumping electrode 4c is opposed to the reference electrode 6c and faces the reference oxygen chamber 15.

The inner first pumping electrode 2b, the detection electrode 6b, and the inner second pumping electrode 4b are each connected to the reference electric potential.

Next, the $NO_2$ sensor unit 42 will be described. The $NO_2$ sensor unit 42 is formed on the insulation layer 23f, which forms the outer surface of the $NO_X$ sensor unit 30A. That is, the insulation layer 23f is partially cut out into a rectangular shape, and the solid electrolyte body for the $NO_2$ sensor 25 is exposed to the surface. A reference electrode 42a and a detection electrode 42b of the $NO_2$ sensor unit 42 are formed on the exposed portion.

Figure 6:
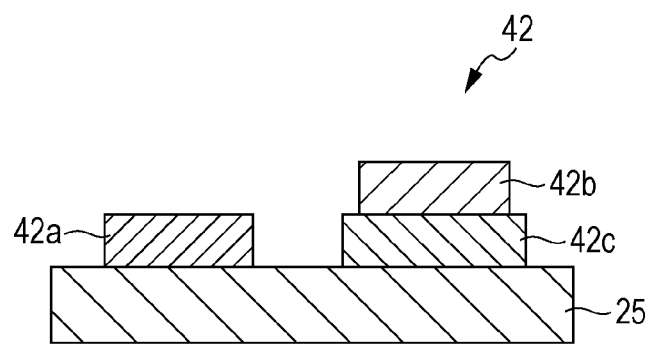
FIG. 6 is a sectional view illustrating a configuration of a $NO_2$ sensor unit.

More specifically, as illustrated in FIG. 6, the reference electrode 42a and an interlayer 42c of the $NO_2$ sensor unit 42 are formed on the solid electrolyte body for $NO_2$ sensor 25. The reference electrode 42a and the interlayer 42c are separated in a lateral direction. The interlayer 42c includes the detection electrode 42b on the surface. The $NO_2$ concentration in the gas to be measured is detected based on a change in electromotive force between the reference electrode 42a and the detection electrode 42b. The solid electrolyte body 25, for example, includes partially stabilized zirconia (YSZ). In FIG. 6, for convenience of explanation, the cross section of the $NO_2$ sensor unit 42 along the lateral direction is illustrated.

The detection electrode 42b contains Au in an amount equal to or more than 70% by mass and does not include a first metal oxide, which will be described below. In view of this, inflammable gas is less likely to burn on the surface of the detection electrode 42b. The interlayer 42c contains a solid electrolyte component having oxygen ion conductivity in an amount equal to or more than 50% by mass. The interlayer 42c includes a first metal oxide, which is at least one kind of metal oxide selected from a group consisting of metal oxides of Co, Mn, Cu, Ni and Ce.

$NO_2$ passes through the detection electrode 42b and reacts with oxygen ion (electrode reaction) at the surface boundary of the detection electrode 42b and the interlayer 42c below. Accordingly, the detection electrode 42b and the interlayer 42c function as a unit for detecting $NO_2$ gas. Here, if the first metal oxide is present at the surface boundary of the detection electrode 42b and the interlayer 42c, sensitivity to a gas other than $NO_2$ gas (such as HC gas) is reduced; therefore, only the selectivity for the $NO_2$ gas improves. The reason therefor is not clear; however, it is probably because the first metal oxide interposed at the surface boundary modifies an electrode reaction site.

The detection electrode 42b does not include the first metal oxide. Consequently, burning of the $NO_2$ gas inside of the detection electrode 42b is suppressed. As a result, the $NO_2$ gas reaching the surface boundary of the detection electrode 42b and the interlayer 42c does not decrease, thus improving detection sensitivity.

From a perspective that the first metal oxide is not included in the detection electrode 42b but included in the neighboring member, it is assumed that the first metal oxide is contained in the solid electrolyte body 25 without using the interlayer 42c. However, the solid electrolyte body 25 includes, for example, partially stabilized zirconia. In view of this, the solid electrolyte body 25 is baked at a high temperature (around 1500° C.). During this baking, there is a possibility that the first metal oxide is volatilized from the solid electrolyte body 25. Accordingly, as in this embodiment, the interlayer 42c is preferably disposed between the solid electrolyte body 25 and the detection electrode 42b.

The first metal oxide included in the interlayer 42c is at least one kind of metal oxide selected from a group consisting of metal oxides of Co, Mn, Cu, Ni and Ce. Especially, when the metal oxide is $Co_3O_4$, a fluctuation in $NO_2$ sensitivity caused by $H_2O$ included in the detected gas to the $NO_2$ gas sensor decreases, which is preferable. The first metal oxide forms as a metal oxide or a complex oxide. The solid electrolyte component included in the interlayer 42c may have the same composition as or may have a different composition from the solid electrolyte body 25 constituting the gas sensor in accordance with the invention.

The interlayer 42c preferably contains the first metal oxide in a proportion of 1 to 50% by mass. If the proportion of contained first metal oxide is less than one % by mass, selectivity for the $NO_2$ gas may not be sufficiently obtained. On the other hand, if the proportion of contained first metal oxide exceeds 50% by mass, the proportion of the solid electrolyte component in the interlayer 42c decreases. Consequently, the oxygen ion conductivity of the interlayer 42c may decrease.

The interlayer 42c is preferably porous because this improves the detection sensitivity of $NO_2$ gas and selectivity for $NO_2$ gas.

Whether the interlayer 42c includes the first metal oxide or not can be confirmed by analyzing the cross section of the $NO_2$ sensor unit using an Electron Probe Microanalyser (EPMA) (usually, an average value from analyses at three locations).

The detection electrode 42b contains Au in an amount equal to or more than 70% by mass. This ensures that the detection electrode 42b is capable of serving as a current collector. If the Au content of the detection electrode 42b is less than 70% by mass, the capability of the detection electrode 42b to serve as a current collector is lowered, thus making the detection of the $NO_2$ gas difficult.

The detection electrode 42b is preferably a porous electrode that includes a second metal oxide, which is at least one kind of metal oxide selected from a group consisting of metal oxides of Zr, Y, Al and Si. This allows the detection electrode 42b to achieve sufficient gas permeability, and allows $NO_2$ to pass through the detection electrode 42b and easily reach the surface boundary of the detection electrode 42b and the interlayer 42c below. As a result, selectivity only for $NO_2$ gas can be ensured. The detection electrode 42b preferably contains the second metal oxide in a proportion of 5 to 30% by mass.

On the other hand, the reference electrode 42a is an electrode having a surface at which inflammable gas burns. The reference electrode 42a is, for example, constituted by a material formed of Pt alone or a material mainly constituted of Pt.

The reference electrode 42a is preferably directly disposed on the solid electrolyte body 25. That is, the interlayer 42c preferable is not present below the reference electrode 42a. As one method for interposing the interlayer 42c between the detection electrode 42b and the solid electrolyte body 25, the detection electrode 42b is formed on the interlayer 42c after the interlayer 42c is formed on the entire surface of the solid electrolyte body 25. In this case, the interlayer 42c is also present below the reference electrode 42a. However, if the reference electrode 42a includes Pt, since the baking temperature of Pt is high (approximately equal to or more than 1400° C.), the first metal oxide included in the interlayer 42c may be volatilized near the reference electrode 42a.

When, for example, the first metal oxide includes Ce, which is difficult to volatilize, the interlayer 42c may be present below the reference electrode 42a.

Next, referring again to FIG. 5, an exemplary configuration of the control device 300 will be described. The control device 300 includes a (analog) control circuit 59 and a microcomputer 60 on a circuit board. The microcomputer 60 controls the entire control device 300. The microcomputer 60 includes a central processing unit (CPU) 61, a RAM 62, a ROM 63, a signal input/output unit 64, an A/D converter 65, and a clock (not shown). The CPU 61 executes a program preliminary stored in, for example, the ROM 63.

The control circuit 59 includes a reference voltage comparison circuit 51, an Ip1 drive circuit 52, a Vs detection circuit 53, the Icp supply circuit 54, an Ip2 detection circuit 55, a Vp2 application circuit 56, a Vh heater drive circuit (a heater circuit) 57, and a $NO_2$ sensor unit electromotive force detection circuit 58, which will be described below.

The control circuit 59 controls the $NO_X$ sensor unit 30A and detects a first pumping current Ip1 and a second pumping current Ip2, which flow in the $NO_X$ sensor unit 30A. The control circuit 59 outputs a detection result to the microcomputer 60.

The $NO_2$ sensor unit electromotive force detection circuit 58 detects $NO_2$ concentration output (an electromotive force) between a pair of electrodes 42a and 42b and outputs the $NO_2$ concentration output to the microcomputer 60.

In detail, the outer first pumping electrode 2c of the $NO_X$ sensor unit 30A is connected to the Ip1 drive circuit 52. The reference electrode 6c is connected to the Vs detection circuit 53 and the Icp supply circuit 54 in parallel. The counterpart second pumping electrode 4c is connected to the Ip2 detection circuit 55 and the Vp2 application circuit 56 in parallel. The heater circuit 57 is connected to the heater 21.

The pair of electrodes 42a and 42b of the $NO_2$ sensor unit 42 are each connected to the $NO_2$ sensor unit electromotive force detection circuit 58.

The circuits 51 to 57 have the respective following functions.

The Ip1 drive circuit 52 supplies the first pumping current Ip1 between the inner first pumping electrode 2b and the outer first pumping electrode 2c and detects the first pumping current Ip1 at that time.

The Vs detection circuit 53 detects a voltage Vs between the detection electrode 6b and the reference electrode 6c and outputs the detection result to the reference voltage comparison circuit 51. The reference voltage comparison circuit 51 compares the reference voltage (for example, 425 mV) and the output from the Vs detection circuit 53 (a voltage Vs) and outputs the comparison result to the Ip1 drive circuit 52. The Ip1 drive circuit 52 controls the direction and the amount of the Ip1 current so that the voltage Vs is equal to the reference voltage. This adjusts the oxygen concentration in the first measuring chamber S1 to a predetermined value so as not to decompose $NO_X$.

The Icp supply circuit 54 supplies a weak current Icp which flows between the detection electrode 6b and the reference electrode 6c. This transports oxygen from the first measuring chamber S1 to the inside of the reference oxygen chamber 15. As a result, the reference electrode 6c is exposed to a predetermined oxygen concentration, which becomes a reference.

The Vp2 application circuit 56 applies a constant voltage Vp2 (for example, 450 mV) to a degree where the $NO_X$ gas in the gas to be measured is decomposed into oxygen and $N_2$ gas between the inner second pumping electrode 4b and the counterpart second pumping electrode 4c. This decomposes the $NO_X$ into nitrogen and oxygen.

The Ip2 detection circuit 55 detects the second pumping current Ip2 flowing in the second pumping cell 4 when the oxygen generated by the decomposition of the $NO_X$ is pumped to the counterpart second pumping electrode 4c side from the second measuring chamber S2 via the second solid electrolyte body 4a.

The Ip1 drive circuit 52 outputs the value of the detected first pumping current Ip1 to the A/D converter 65. The Ip2 detection circuit 55 outputs the value of the detected second pumping current Ip2 to the A/D converter 65.

The A/D converter 65 converts these values into digital values and outputs the digital values to the CPU 61 via the signal input/output unit 64.

Next, one exemplary control using the control circuit 59 will be described. First, upon start of the engine, electric power is supplied from an external power source to the deterioration diagnosis device for determining a deterioration degree of an oxidation catalyst 250. Then, the heater circuit 57 operates the heater 21. The heater circuit 57 heats the first pumping cell 2, the oxygen concentration detection cell 6, and the second pumping cell 4 to an activation temperature. The Icp supply circuit 54 flows a weak current Icp between the detection electrode 6b and the reference electrode 6c. This transports oxygen from the first measuring chamber S1 to the inside of the reference oxygen chamber 15. As a result, the reference electrode 6c is exposed to a predetermined oxygen concentration, which becomes a reference.

When the $NO_X$ sensor unit 30A is heated to an appropriate temperature by the heater 21, accordingly, the temperature of the $NO_2$ sensor unit 42 on the $NO_X$ sensor unit 30A also rises to a desired temperature.

When each cell is heated to the activation temperature, the first pumping cell 2 pumps oxygen in the gas to be measured (exhaust gas) which has been introduced into the first measuring chamber S1 from the inner first pumping electrode 2b to the outer first pumping electrode 2c.

At this time, the oxygen concentration inside of the first measuring chamber S1 assumes a value corresponding to a voltage Vs developed between electrodes of the oxygen concentration detection cell 6 (a voltage across the terminal s). In view of the above, the Ip1 drive circuit 52 controls the first pumping current Ip1 flowing in the first pumping cell 2 so that the voltage Vs across the electrodes becomes the reference voltage. This adjusts the oxygen concentration in the first measuring chamber S1 to a concentration so as not to decompose the $NO_X$.

The gas to be measured in which the oxygen concentration has been adjusted further flows toward the second measuring chamber S2. As a voltage between electrodes of the second pumping cell 4 (a voltage between terminal s), the Vp2 application circuit 56 applies a constant voltage Vp2 (a voltage higher than a control voltage value of the oxygen concentration detection cell 6, for example, 450 mV) to the degree that the $NO_X$ gas in the gas to be measured is decomposed into oxygen and $N_2$ gas. This decomposes the $NO_X$ into nitrogen and oxygen. The second pumping current Ip2 flows through the second pumping cell 4 so that the oxygen generated by the decomposition of the $NO_X$ is pumped from the second measuring chamber S2. In this respect, the second pumping current Ip2 and the $NO_X$ concentration are in linear relationship. Thus, the $NO_X$ concentration in the gas to be measured can be detected based on the second pumping current Ip2 detected by the Ip2 detection circuit 55.

The $NO_2$ concentration in the gas to be measured can be detected by detecting the $NO_2$ concentration output (the electromotive force) between the pair of electrodes 42a and 42b by the $NO_2$ sensor unit electromotive force detection circuit 58. The $NO_2$ concentration is calculated by storing an $NO_2$ concentration conversion value based on an electromotive force between the electrodes 42a and 42b (it is also possible to use a changing rate (sensitivity) between a base electromotive force value when the $NO_2$ concentration is 0 and an electromotive force value when $NO_2$ is present) in the microcomputer 60. This calculation process will be described below.

Figure 7:
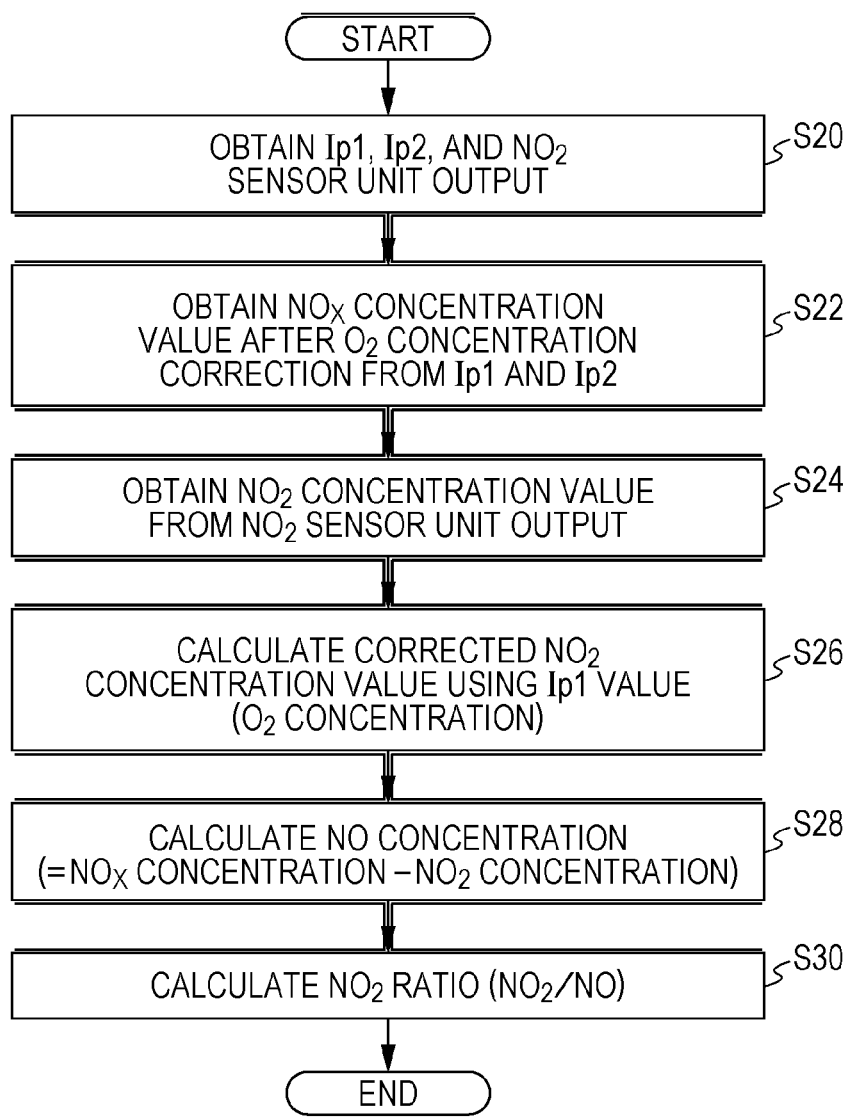
FIG. 7 is a diagram illustrating a processing flow of calculating various gas concentrations by the control device of the multi-gas sensor.

Next, a processing flow of calculating various gas concentrations by the microcomputer 60 of the control device 300 will be described with reference to FIG. 7.

Figure 8:
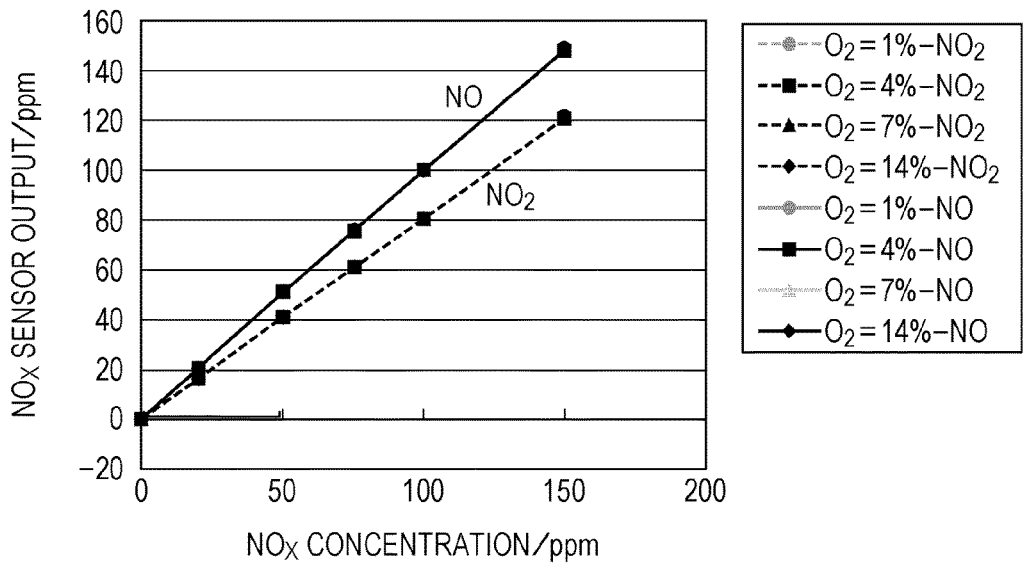
FIG. 8 is a graph illustrating a relationship between Ip2 and $NO_X$ concentration after correction of $O_2$ concentration.

First, the microcomputer 60 obtains the value of the first pumping current Ip1, the value of the second pumping current Ip2, and the $NO_2$ concentration output (the electromotive force) (Step S20). Next, the microcomputer 60 calculates a $NO_X$ concentration value after $O_2$ concentration correction based on Ip1 and Ip2 (Step S22). Even if the $NO_X$ concentration is the same, the higher the $O_2$ concentration in the gas to be measured, the smaller the Ip2 value. In view of this, the microcomputer 60 corrects the calculated $NO_X$ concentration value to have a true value depending on the $O_2$ concentration. The current Ip1 is proportional to the $O_2$ concentration in the gas to be measured. In this manner, the $O_2$ concentration can be obtained from the Ip1. FIG. 8 illustrates a relationship between the Ip2 and the $NO_X$ concentration after the $O_2$ concentration correction.

Figure 9:
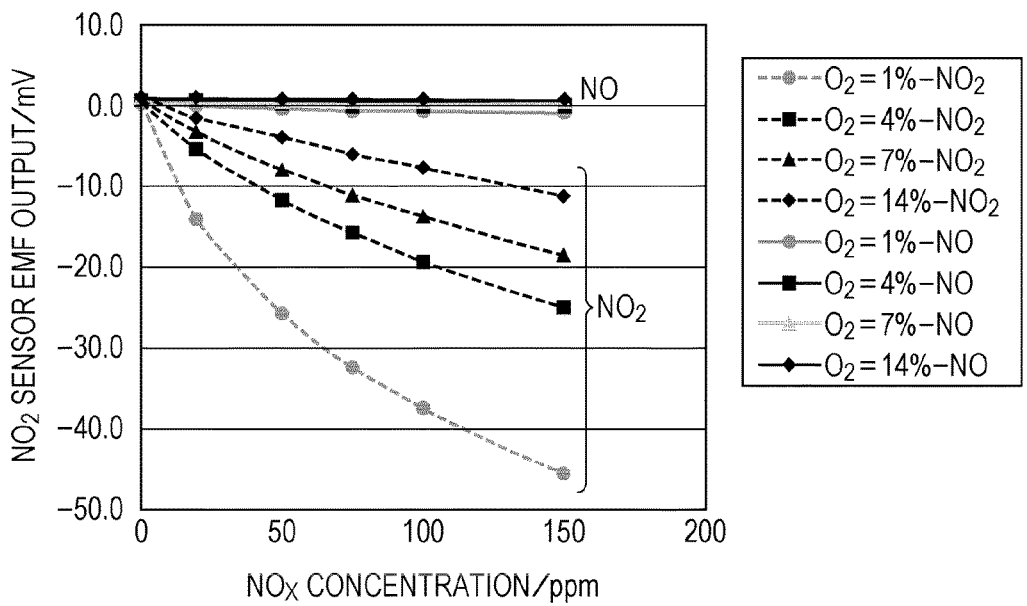
FIG. 9 a graph illustrating a relationship between an EMF output from a $NO_2$ sensor and NO concentration and $NO_2$ concentration.
Figure 10:
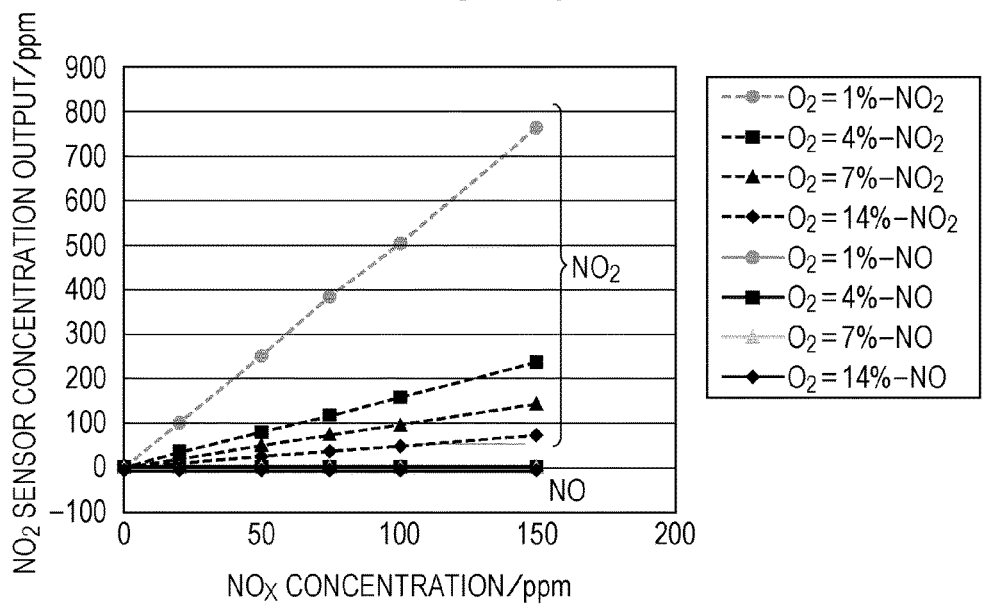
FIG. 10 is a graph illustrating a relationship between an output of concentration conversion of $NO_2$ sensor and NO concentration and $NO_2$ concentration before $O_2$ concentration correction.
Figure 11:
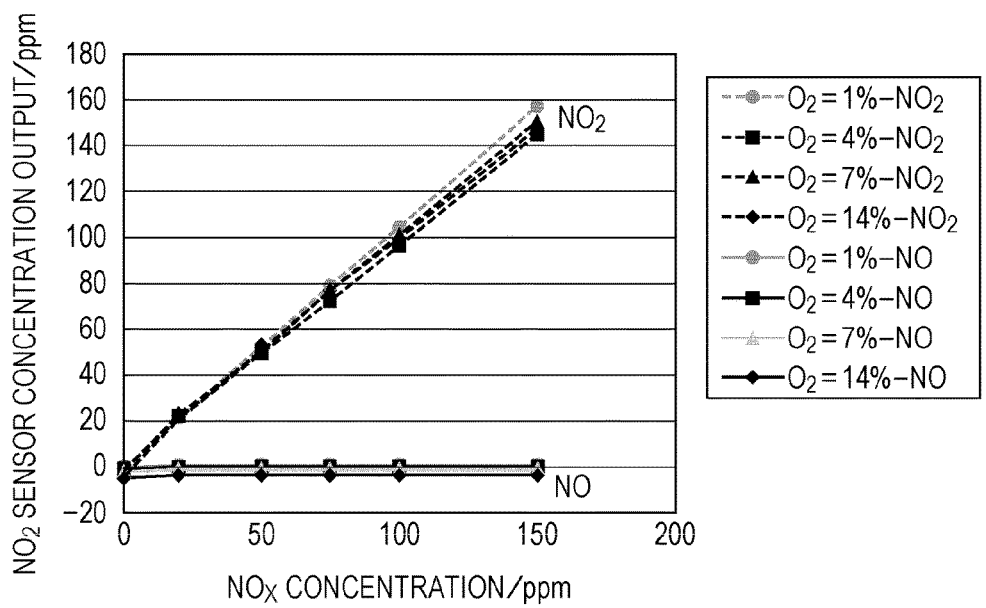
FIG. 11 is a graph illustrating a relationship between an output of concentration conversion of a $NO_2$ sensor and NO concentration and $NO_2$ concentration after $O_2$ concentration correction.

Next, the microcomputer 60 calculates the $NO_2$ concentration value after the $O_2$ concentration correction based on Ip1 and the $NO_2$ concentration output (Step S24). That is, even if the $NO_2$ concentration is the same, the higher the $O_2$ concentration in the gas to be measured, the smaller the $NO_2$ concentration output value. In view of this, the microcomputer 60 corrects the calculated $NO_2$ concentration value to have a true value depending on the $O_2$ concentration (Step S26). FIG. 9 illustrates a relationship between the EMF output of the $NO_2$ sensor before $O_2$ concentration correction and the NO concentration and the $NO_2$ concentration. It can be seen that the $NO_2$ sensor unit 42 does not have sensitivity to NO. FIG. 10 illustrates a relationship between the concentration conversion output of the $NO_2$ sensor before the $O_2$ concentration correction and the NO concentration and the $NO_2$ concentration. It can be seen that even if the $NO_2$ concentration is the same, the higher the $O_2$ concentration in the gas to be measured, the smaller the $NO_2$ concentration output value. FIG. 11 illustrates a relationship between the concentration conversion output of the $NO_2$ sensor after the $O_2$ concentration correction and the NO concentration and the $NO_2$ concentration.

Next, the microcomputer 60 calculates the NO concentration where NO concentration=($NO_X$ concentration–$NO_2$ concentration) (Step S28), and calculates the $NO_2$ ratio where $NO_2$ ratio=($NO_2$ concentration/NO concentration) (Step S30).

The microcomputer 60 corresponds to "the NO concentration calculation unit" of the invention. The $NO_2$ ratio corresponds to "the evaluation value" of the invention.

Figure 12:
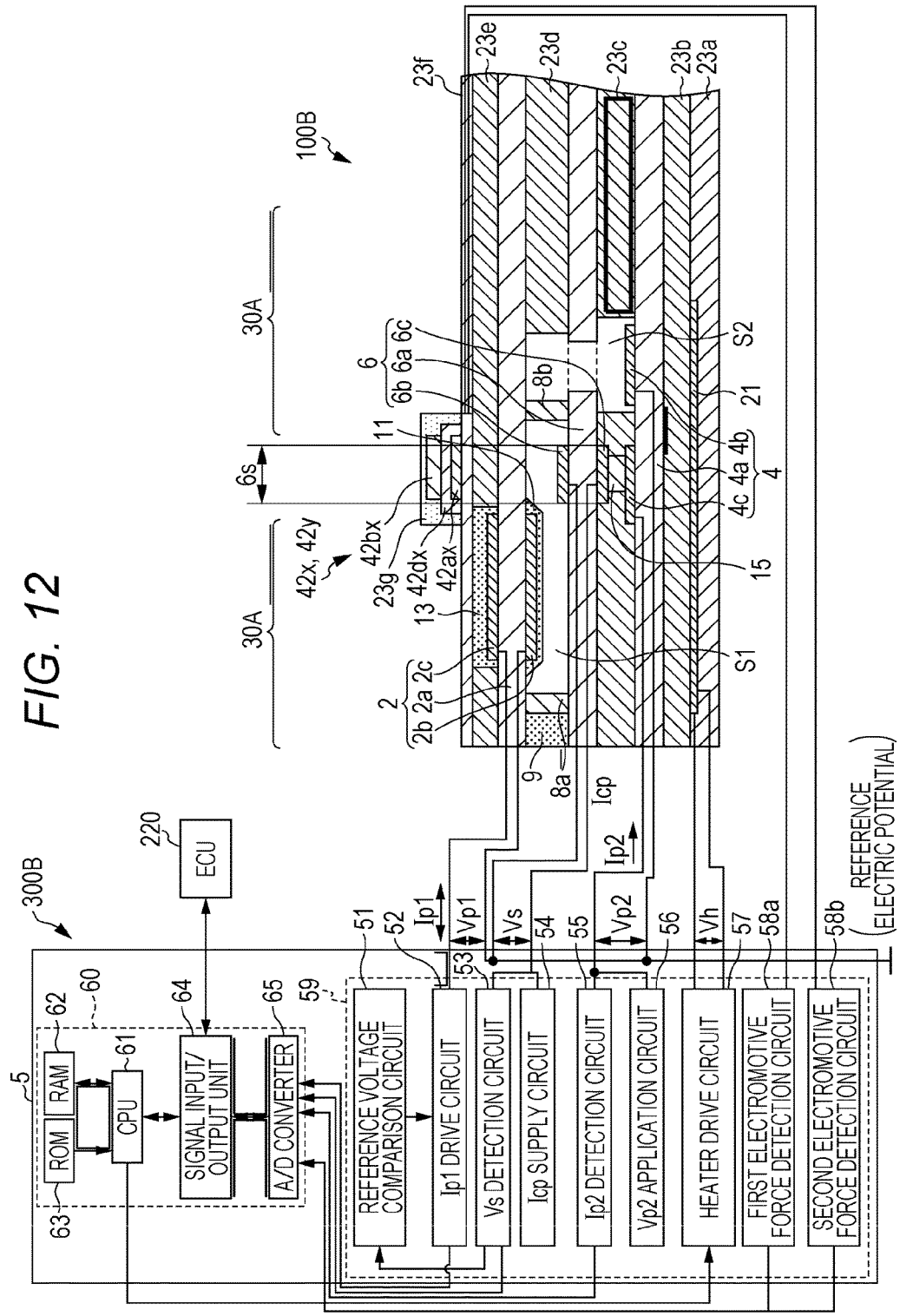
FIG. 12 is a block diagram illustrating a configuration of the multi-gas sensor and the gas sensor control device according to a second embodiment of the invention.
Figure 13:
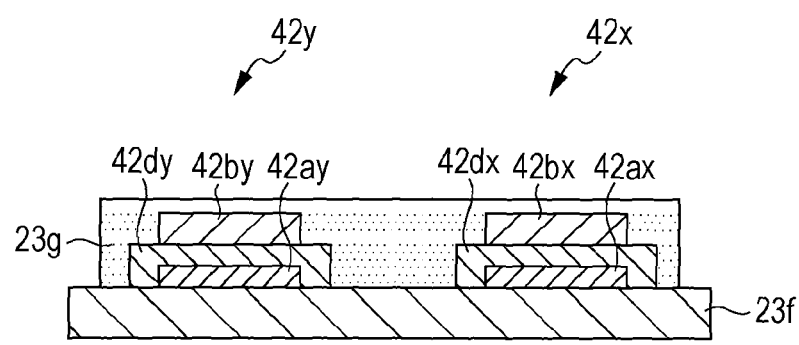
FIG. 13 is a sectional view illustrating a configuration of a first $NO_2$ sensor unit and a second $NO_2$ sensor unit.

Next, a multi-gas sensor according to a second embodiment will be described with reference to FIG. 12 and FIG. 13. FIG. 12 is a sectional view of a multi-gas sensor 200B (a multi-gas sensor element unit 100B) according to the second embodiment along the longitudinal direction (the axial direction). FIG. 13 is a sectional view illustrating the configuration of $NO_2$ sensor units 42x and 42y along the width direction of the multi-gas sensor element unit 100B. Members of the multi-gas sensor 200B other than the multi-gas sensor element unit 100B are the same as the members of the multi-gas sensor 200A according to the first embodiment. Thus, the illustration of these members is omitted.

The multi-gas sensor element unit 100B of the multi-gas sensor 200B according to the second embodiment is the same as the multi-gas sensor element unit 100A, except that the configuration of the $NO_2$ sensor unit is different and the solid electrolyte body for the $NO_2$ sensor 25 is not included Like reference numerals designate identical elements throughout the embodiments, and therefore the following description will not further elaborate on such elements. The multi-gas sensor 200B includes two $NO_2$ sensor units. Thus, a control device 300B includes two circuits: a first electromotive force detection circuit 58a and a second electromotive force detection circuit 58b as an electromotive force detection circuit for $NO_2$ sensor unit. Except for this, the control device 300B has the same configuration as the control device 300. Like reference numerals designate identical elements throughout the embodiments, and therefore the following description will not further elaborate on such elements.

As illustrated in FIG. 13, the multi-gas sensor element unit 100B includes the first $NO_2$ sensor unit 42x and the second $NO_2$ sensor unit 42y separated from one another in the width direction.

The first $NO_2$ sensor unit 42x and the second $NO_2$ sensor unit 42y are formed on the insulation layer 23f, which is the outer surface of the $NO_X$ sensor unit 30A. More specifically, the first $NO_2$ sensor unit 42x includes a reference electrode 42ax on the insulation layer 23f. The top surface and the side surfaces of the first reference electrode 42ax are covered with a first solid electrolyte body 42dx. A first detection electrode 42bx is formed on the surface of the first solid electrolyte body 42dx. $NO_2$ concentration in a measured gas is detected based on changes in the electromotive force between the first reference electrode 42ax and the first detection electrode 42bx.

Similarly, the second $NO_2$ sensor unit 42y includes a second reference electrode 42ay on the insulation layer 23f. The top surface and the side surfaces of the second reference electrode 42ay are covered with a second solid electrolyte body 42dy. A second detection electrode 42by is formed on the surface of the second solid electrolyte body 42dy.

The first $NO_2$ sensor unit 42x and the second $NO_2$ sensor unit 42y are integrally covered with a protective layer 23g including a porous material.

The protective layer 23g prevents poisoning substances from accumulating on the first detection electrode 42bx and the second detection electrode 42by. The protective layer 23g adjusts the diffusion speed of the gas to be measured which has flowed from the outside to the first $NO_2$ sensor unit 42x and the second $NO_2$ sensor unit 42y. The material forming the protective layer 23g, for example, may be at least one kind of material selected from the group consisting of alumina (aluminum oxide), spinel ($MgAl_2O_4$), silica alumina and mullite. The diffusion speed of the gas to be measured is adjusted by adjusting, for example, the thickness, the particle diameter, the particle size distribution, the porosity, and/or the mixing ratio of the protective layer 23g.

The protective layer 23g may be disposed in a manner similar to the above-described embodiment. The first $NO_2$ sensor unit 42x, the second $NO_2$ sensor unit 42y, or similar member may be exposed without disposing the protective layer 23g. The presence or absence of the protective layer 23g is not particularly limited.

The first detection electrode 42bx and the second detection electrode 42by can be formed of a material mainly constituted of Au (for example, a material containing Au in an amount equal to or more than 70% by mass). The first detection electrode 42bx and the second detection electrode 42by can be formed of Pt alone or a material mainly constituted of Pt (for example, a material containing Pt in an amount equal to or more than 70% by mass). The first detection electrode 42bx and the second detection electrode 42by are located where $NO_2$ gas is less likely to burn on their respective surfaces. $NO_2$ passes through the detection electrode 42bx (42by) and reaches the surface boundary of the detection electrode 42bx (42by) and the underlying reference electrode 42ax (42ay). The $NO_2$ reacts with oxygen ion at this surface boundary (electrode reaction). This allows detecting the concentration of $NO_2$.

The first solid electrolyte body 42dx and the second solid electrolyte body 42dy, for example, include partially stabilized zirconia (YSZ). The first reference electrode 42ax and the second reference electrode 42ay may have a composition similar to the composition of the reference electrode 42a. The first detection electrode 42bx and the second detection electrode 42by may have a composition similar to the composition of the detection electrode 42b. The first NO₂ sensor unit 42x and the second NO₂ sensor unit 42y do not include an interlayer.

Here, in this embodiment, the temperature of the oxygen concentration detection cell (corresponding to the "temperature detector" of the invention) 6 is measured. Based on this measured temperature, the heater 21 is heated. In view of the above, the temperature of the multi-gas sensor element unit 100B is kept at the most stable value adjacent to the oxygen concentration detection cell 6. Because the multi-gas sensor element unit 100B is distant from the oxygen concentration detection cell 6 in the axial direction, the change in temperature of multi-gas sensor element unit 100B becomes larger with fluctuation in the external temperature.

Accordingly, the first NO₂ sensor unit 42x and the second NO₂ sensor unit 42y preferably at least partially overlap with a position 6s of the oxygen concentration detection cell 6 as viewed from the axial direction. In this case, the temperatures of the first NO₂ sensor unit 42x and the second NO₂ sensor unit 42y are kept constant within a predetermined range. As a result, the NO₂ measurement accuracy improves. The position 6s of the oxygen concentration detection cell 6 is an overlapping portion of the detection electrode 6b and the reference electrode 6c included in the oxygen concentration detection cell 6 (in this embodiment, both electrodes have approximately the same dimension and are disposed at approximately the same position). Similarly, the NO₂ sensor unit is disposed at the overlapping portion of the detection electrode 6b and the reference electrode 6c.

Figure 14:
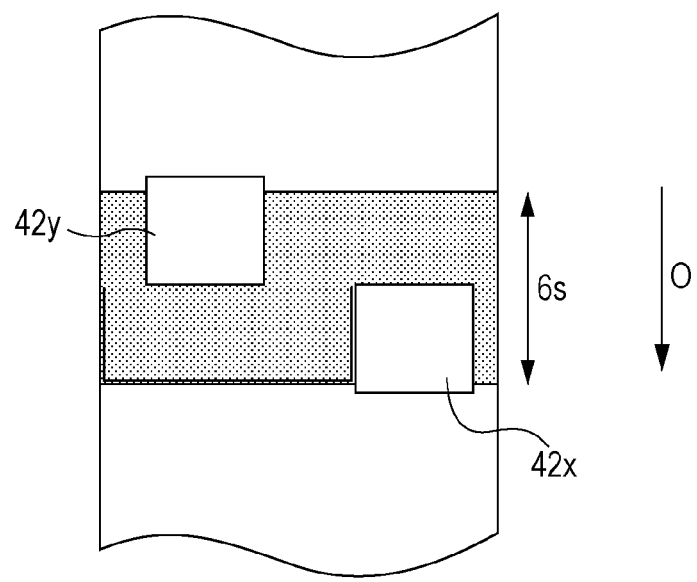
FIG. 14 is a top view illustrating another example where the first $NO_2$ sensor unit and the second $NO_2$ sensor unit overlap with an oxygen concentration detection cell in the multi-gas sensor according to the second embodiment.
Figure 15:
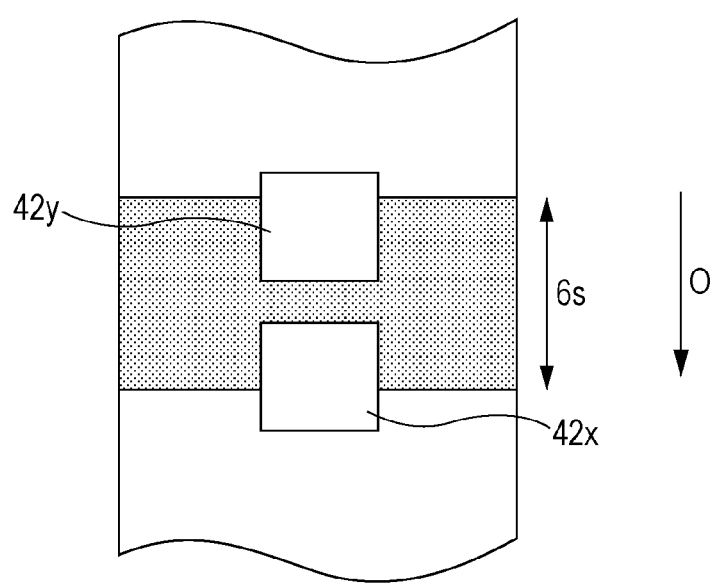
FIG. 15 is a top view illustrating yet another example where the first $NO_2$ sensor unit and the second $NO_2$ sensor unit overlap with the oxygen concentration detection cell in the multi-gas sensor according to the second embodiment.

The overlapping state of the first NO₂ sensor unit 42x or the second NO₂ sensor unit 42y with the oxygen concentration detection cell 6 is not limited to the above-described state. For example, as illustrated in FIG. 14, the first NO₂ sensor unit 42x and the second NO₂ sensor unit 42y may be separated from one another in the width direction of the multi-gas sensor element unit 100B (the direction vertical to an axis O direction). The front end side of the first NO₂ sensor unit 42x may protrude with respect to the front end of the position 6s. The rear end side of the second NO₂ sensor unit 42y may protrude with respect to the rear end of the position 6s. As illustrated in FIG. 15, the first NO₂ sensor unit 42x and the second NO₂ sensor unit 42y may be separated from one another in the ax axis O direction of the multi-gas sensor element unit 100B. The front end side of the first NO₂ sensor unit 42x may protrude with respect to the front end of the position 6s. The rear end side of the second NO₂ sensor unit 42y may protrude with respect to the rear end of the position 6s.

In the second embodiment, the reason for disposing two NO₂ sensor units: the first NO₂ sensor unit 42x and the second NO₂ sensor unit 42y is as follows. That is, the NO₂ sensor unit detects not only NO₂ but also another gas constituent (especially, inflammable gas such as propylene). In view of this, if a disturbance (interfering) gas other than NO₂ is included in the detected gas, the detection accuracy of NO₂ is reduced. Therefore, two NO₂ sensor units with a different sensitivity ratio to NO₂ from one another are preferably disposed. In this case, the two NO₂ sensor units detect two unknown concentrations of NO₂ gas and disturbance gas at different sensitivities. In view of the above, the concentration of the NO₂ gas and the disturbance gas can be calculated. Here, "the sensitivity ratio of the NO₂ sensor unit to NO₂" is a ratio of the detection sensitivity of NO₂ to that of all gases detected by the NO₂ sensor unit (including NO₂ and the following disturbance gas).

That is, the sensor output of the NO₂ sensor unit is expressed as F (x, y, D) assuming that x is NO₂ concentration, y is a disturbance gas concentration output, and D is the O₂ concentration output. The use of the two NO₂ sensor units with different sensitivity ratios allows obtaining the following two formulas: F1 (mx, ny, D) and F2 (sx, ty, D), where m, n, s, and t are coefficients. F1, F2, and D are obtained from the sensor output. Accordingly, the only two unknown variables (x, y) may be solved from the two formulas. Specifically, the formulas can be calculated by removing y from the two formulas and obtaining x as in formulas (1) and (2), which will be described below. For application of this disclosure, obtaining the NO₂ concentration output where influence of the disturbance gas has been removed is sufficient. Obtaining the disturbance gas concentration is not required.

A method for changing the sensitivity ratio of the NO₂ sensor unit for NO₂ adds co-electrolyte (the constituent of the solid electrolyte body) or a precious metal such as Pt or Pd to the detection electrode. That is, simply changing the amount of co-electrolyte or precious metal added to the first detection electrode 42bx and the second detection electrode 42by changes the sensitivity ratio of NO₂ between the first detection electrode 42bx and the second detection electrode 42by. When the amount of co-electrolyte or precious metal to be added is increased, the sensitivity ratio tends to be large.

Here, the sensitivity of the NO₂ sensor unit differs depending on the type of disturbance gas (inflammable gas). In view of above, usually, if the constituent of the disturbance gas is not known, the calculation cannot be performed. However, the following point has been demonstrated by the inventor. That is, for example, using the NO₂ sensor unit having a sensitivity ratio 1 and the NO₂ sensor unit having a sensitivity ratio 2, the relational expression between the concentration of a known disturbance gas (propylene) and the concentration of NO₂ is preliminarily generated. Even if the type of the disturbance gas differs, the trend of the relational expression is the same.

Accordingly, even if the constituent of the disturbance gas is unknown, the calculation can be performed. That is, for example, whether the inflammable gas is propylene or another inflammable gas (for example, $C_3H_8$ or $C_4H_8$), the ratio of detection value of each gas in the first NO₂ sensor unit 42x and the second NO₂ sensor unit 42y is almost constant.

Next, details of detection of NO₂ and the disturbance gas by the first NO₂ sensor unit 42x and the second NO₂ sensor unit 42y and the calculation of the concentrations of the NO₂ gas and the disturbance gas will be described.

An electromotive force according to the NO₂ concentration included in the gas to be measured is generated between the first reference electrode 42ax and the first detection electrode 42bx of the first NO₂ sensor unit 42x. The first electromotive force detection circuit 58a detects an electromotive force between the first reference electrode 42ax and the first detection electrode 42bx as a first NO₂ electromotive force. Similarly, an electromotive force according to the NO₂ concentration is also generated between the second reference electrode 42ay and the second detection electrode 42by of the second NO₂ sensor unit 42y. The second electromotive force detection circuit 58b detects an electromotive force between the second reference electrode 42ay and the second detection electrode 42by as a second NO₂ electromotive force.

The ROM 63 of the microcomputer 60 stores various data (relational expressions) described below. The CPU 61 reads the various data from the ROM 63 and performs various arithmetic operations using the value of the first pumping current Ip1, the value of the second pumping current Ip2, the first $NO_2$ electromotive force, and the second $NO_2$ electromotive force.

More particularly, the ROM 63 stores "output relational expression between first $NO_2$ electromotive force and first $NO_2$ concentration", "output relational expression between second $NO_2$ electromotive force and second $NO_2$ concentration", "output relational expression between first pumping current Ip1 and $O_2$ concentration", "output relational expression between second pumping current Ip2 and $NO_X$ concentration", "output relational expression between first $NO_2$ concentration output & second $NO_2$ concentration output & $O_2$ concentration output and corrected $NO_2$ concentration" (correction formula (1): see below), and "output relational expression between $NO_X$ concentration output & corrected $NO_2$ concentration output and $NO_2/NO$ ratio" (correction formula (2): see below).

The various data may be set as predetermined relational expressions as described above. It is only necessary that the various data (for example, relational expressions) is data that allows calculating various gas concentrations using the output value of the sensor. The various data may be, for example, a table. Alternatively, the various data may be data regarding a gas concentration value (for example, relational expressions or tables) preliminarily obtained using a known gas model.

"Output relational expression between first $NO_2$ electromotive force and first $NO_2$ concentration" and "output relational expression between second $NO_2$ electromotive force and second $NO_2$ concentration" are formulas expressing the relationships between the $NO_2$ electromotive forces output from the first $NO_2$ sensor unit 42x and the second $NO_2$ sensor unit 42y and the $NO_2$ concentration output regarding the $NO_2$ concentration of the gas to be measured.

"Output relational expression between first pumping current Ip1 and $O_2$ concentration" is a formula expressing the relationship between the first pumping current Ip1 and the $O_2$ concentration of the gas to be measured.

"Output relational expression between second pumping current Ip2 and $NO_X$ concentration" is a formula expressing the relationship between the second pumping current Ip2 and the $NO_X$ concentration of the gas to be measured.

"Output relational expression between first $NO_2$ concentration output & second $NO_2$ concentration output & $O_2$ concentration output and corrected $NO_2$ concentration" is a formula expressing the relationship between the $NO_2$ concentration outputs (first and second) affected by the oxygen concentration and various inflammable gas concentrations and the corrected $NO_2$ concentration output where the influence of the oxygen concentration and the various inflammable gas concentrations is removed.

"Output relational expression between $NO_X$ concentration output & corrected $NO_2$ concentration output and $NO_2/NO$ ratio" is a formula for calculating the $NO_2/NO$ ratio from the $NO_X$ concentration output and the $NO_2$ concentration output where the influence of the various inflammable gas concentrations is removed.

Next, arithmetic operations obtaining the $NO_X$ concentration and the $NO_2/NO$ ratio using the first pumping current Ip1, the second pumping current Ip2, the first $NO_2$ electromotive force EMF, and the second $NO_2$ electromotive force EMF will be described. The arithmetic operations are performed in the CPU 61 of the microcomputer 60.

When the first pumping current Ip1, the second pumping current Ip2, the first $NO_2$ electromotive force, and the second $NO_2$ electromotive force are input, the CPU 61 performs the arithmetic operations obtaining the $O_2$ concentration output, the $NO_X$ concentration output, the first $NO_2$ concentration output, and the second $NO_2$ concentration output. Specifically, the CPU 61 calls "output relational expression between first $NO_2$ electromotive force and first $NO_2$ concentration", "output relational expression between second $NO_2$ electromotive force and second $NO_2$ concentration", "output relational expression between first pumping current Ip1 and $O_2$ concentration", and "output relational expression between second pumping current Ip2 and $NO_X$ concentration" from the ROM 63. The CPU 61 performs a process calculating each concentration output using these relational expressions.

"Output relational expression between first $NO_2$ electromotive force and first $NO_2$ concentration" and "output relational expression between second $NO_2$ electromotive force and second $NO_2$ concentration" are formulas set so that the $NO_2$ concentration in the gas to be measured and the $NO_2$ concentration conversion output of the sensor have approximately a linear relationship in all ranges of EMF where the first $NO_2$ sensor unit 42x and the second $NO_2$ sensor unit 42y can output in an operating environment. Converting with such conversion formulas allows calculation using changes in gradients and offset in the correction formula performed later.

When the $O_2$ concentration output, the $NO_X$ concentration output, the first $NO_2$ concentration output, and the second $NO_2$ concentration output are obtained, the CPU 61 performs an operation using the correction formula described below. Thus, the CPU 61 obtains the $NO_2$ concentration and the $NO_2/NO$ ratio of the gas to be measured.

$$x = F(A,B,D) = (eA-c)*(jB-h-fA+d)/(eA-c-iB+g)+fA-d \quad \text{Correction formula (1):}$$

$$NO_2/NO = x/(C-axax) \quad \text{Correction formula (2):}$$

Here, x represents the $NO_2$ concentration. A represents the first $NO_2$ concentration output. B represents the second $NO_2$ concentration output. C represents the $NO_X$ concentration output. D represents the $O_2$ concentration output. F in the formula (1) represents that x is a function of (A, B, D). "a" represents a correction coefficient. "c", "d", "e", "f", "g", "h", "i", and "j" are coefficients calculated using $O_2$ concentration output D (coefficients determined by D). The first $NO_2$ concentration output (A), the second $NO_2$ concentration output (B), the $NO_X$ concentration output (C), and the $O_2$ concentration output (D) are substituted in the above-described correction formula, and the formula is executed. Thus, the $NO_2$ concentration and the $NO_2/NO$ ratio of the gas to be measured and similar parameters are obtained.

The correction formula (1) is a formula determined based on the properties of the first $NO_2$ sensor unit 42x and the second $NO_2$ sensor unit 42y. The correction formula (2) is a formula determined based on the property of the $NO_X$ sensor unit 30A. These formulas are exemplary correction formulas. The correction formula and/or the coefficient or similar parameter may be appropriately changed according to a gas detection property. Whether the oxidation catalyst is deteriorated or not can be determined using not only the $NO_2/NO$ ratio but also appropriate values such as $NO_2/NOx$, $NO/NOx$, $NO_2$ concentration, and NO concentration.

Next, the actual $NO_2$ concentration output performed by the multi-gas sensor 200B according to the second embodiment before and after the correction process using the correction formulas (1) and (2) will be described.

Figure 16A:
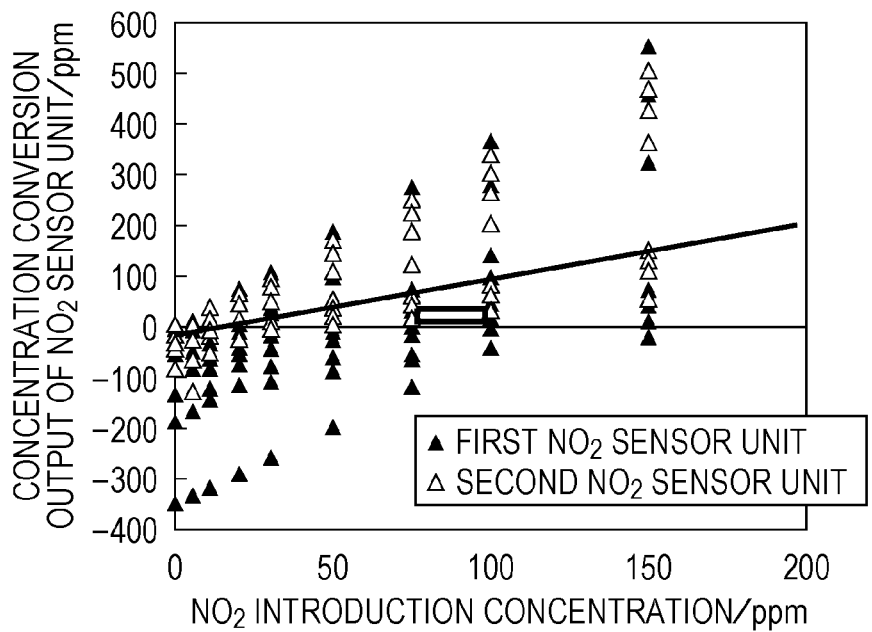
FIG. 16A and FIG. 16B are graphs illustrating calculation results of concentrations of corrected $NO_2$ in the case of using $C_3H_6$ as an inflammable gas species.

FIG. 16A is a graph plotting the concentration conversion output of the first $NO_2$ sensor unit and the second $NO_2$ sensor unit when $NO_2$=0-150 ppm is introduced under the conditions of $O_2$=2, 7, or 15% and $C_3H_6$=0, 20, 50, or 100 ppm. The concentration conversion outputs of the first $NO_2$ sensor unit 42x and the second $NO_2$ sensor unit 42y vary significantly due to influence of the $C_3H_6$ concentration and the $O_2$ concentration.

Figure 16B:
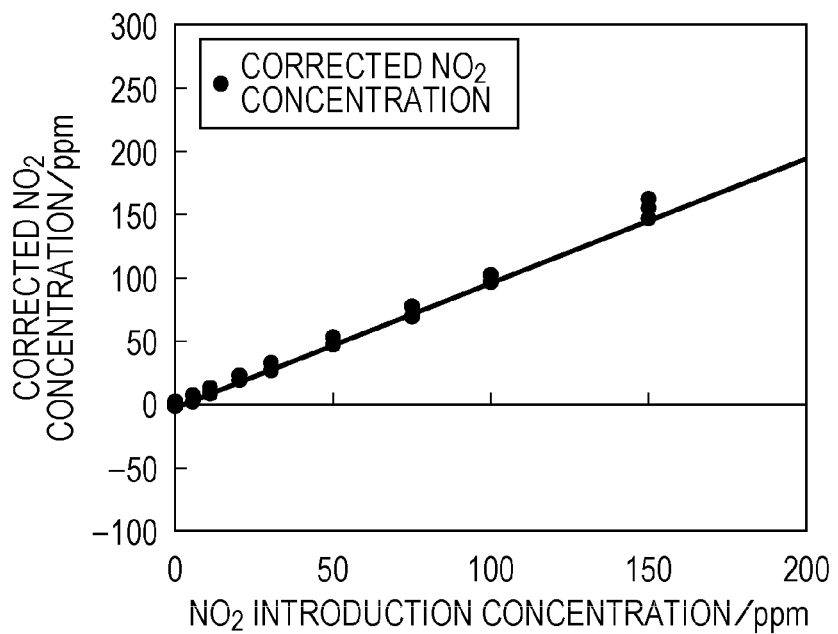

Meanwhile, FIG. 16B is a graph plotting the corrected $NO_2$ concentration output, which is obtained by substituting the values of the $NO_2$ concentration output and the $O_2$ concentration output in the correction formula (1), relative to the $NO_2$ introduction concentration. The present inventor found that use of the correction formula (1) allows calculation of an accurate $NO_2$ concentration where the influence of $C_3H_6$ and $O_2$ is removed.

The corrected $NO_2/NO$ ratio can be calculated with the correction formula (2) obtained from the $NO_X$ sensor output characteristics.

Figure 17A:
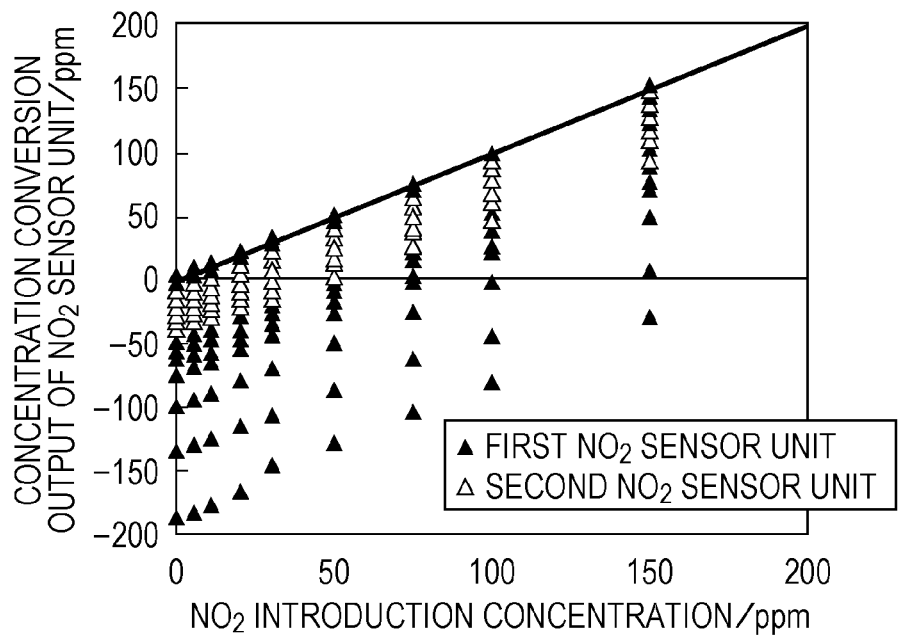
FIG. 17A and FIG. 17B are graphs illustrating the calculation results of the concentrations of the corrected $NO_2$ in the case of using an inflammable gas other than $C_3H_6$.
Figure 17B:
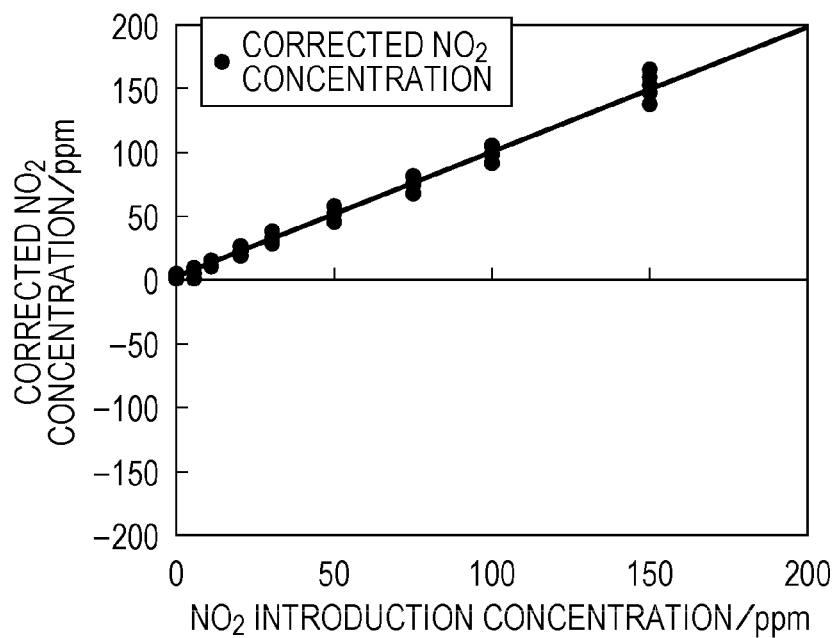

FIG. 16A and FIG. 16B are calculation results of the concentration of corrected $NO_2$ in case of using $C_3H_6$ as an inflammable gas species. However, in an actual exhaust gas environment, various types of inflammable gases exist besides $C_3H_6$. FIG. 17A and FIG. 17B illustrate the calculation results of the corrected $NO_2$ concentration output when another inflammable gas coexists. The formula used for the correction is a formula created based on the relationship between $NO_2$ and $C_3H_6$ completely the same as the formula used in FIG. 16A and FIG. 16B.

FIG. 17A is a graph plotting the concentration conversion output of the first $NO_2$ sensor unit and the second $NO_2$ sensor unit when $NO_2=0-150$ ppm is introduced under the conditions of $O_2=7\%$ and various inflammable gases=0, 20, 50, or 100 ppm. The inflammable gases are $C_3H_6$, $C_3H_8$, $C_4H_8$, $C_4H_{10}$, CO and NO, respectively. The concentration conversion outputs of the first $NO_2$ sensor unit 42x and the second $NO_2$ sensor unit 42y vary significantly by the influence of each inflammable gas concentration and the $O_2$ concentration.

Meanwhile, FIG. 17B is a graph plotting the corrected $NO_2$ concentration output, which is obtained by substituting the values of the $NO_2$ concentration output and the $O_2$ concentration output in the correction formula (1), relative to the $NO_2$ introduction concentration. Use of the correction formula (1) was found to allow calculation of an accurate $NO_2$ concentration where the influence of various types of inflammable gases is removed even if such inflammable gases are present.

Figure 18:
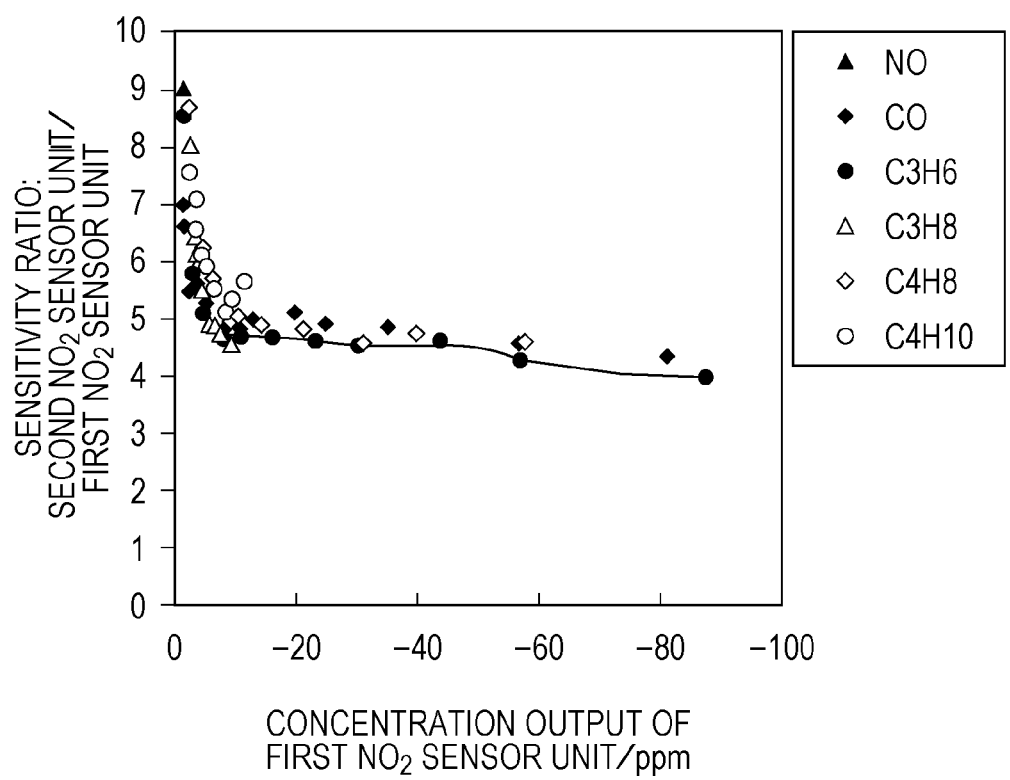
FIG. 18 is a graph plotting an output ratio of the first $NO_2$ sensor unit to the second $NO_2$ sensor unit for each inflammable gas relative to the output of the first $NO_2$ sensor unit.

FIG. 18 is a graph plotting an output ratio of the first $NO_2$ sensor unit 42x to the second $NO_2$ sensor unit 42y for each inflammable gas relative to the output of the first $NO_2$ sensor unit 42x. It was found from this graph that even if the type of the inflammable gas changes, the output ratio of the first $NO_2$ sensor unit 42x to the second $NO_2$ sensor unit 42y relative to the inflammable gas exhibits an almost similar trend. That is, even if the type of the inflammable gas changes, the influence rate of the inflammable gas relative to the two $NO_2$ sensor outputs are similar. In view of the above, if the correction formula is created using any of inflammable gases, the $NO_2$ concentration can be corrected even if another inflammable gas coexists in the gas to be measured. The multi-gas sensor 200B according to the second embodiment has the above-described output characteristics to various inflammable gases and $NO_2$. Accordingly, this multi-gas sensor 200B can calculate the $NO_2$ concentration where the influence of various inflammable gases is removed.

As described above, use of the multi-gas sensor 200B and the correction method according to the second embodiment allows precise correction calculation on $NO_2$ concentration even in an environment where various inflammable gases coexist and the oxygen concentration changes. Calculating the $NO_2$ sensor output and the $NO_X$ sensor output allows separately detecting $NO_2$ and NO.

The present invention is not limited to the above embodiments. Various modifications and variations of the embodiments described above will be apparent to those skilled in the art.

For example, in the above embodiments, the microcomputer 60 disposed in the control device 300 calculates the NO concentration and the $NO_2$ ratio. The calculated $NO_2$ ratio is output to the deterioration judgment unit 221 in the ECU 220. However, this should not be construed in a limiting sense. The NO concentration calculation unit may be disposed in the ECU 220, such that the $NO_2$ concentration and the $NO_X$ concentration after the $O_2$ concentration correction calculated by the microcomputer 60 may be output to the NO concentration calculation unit in the ECU 220. In that case, the NO concentration calculation unit may calculate the NO concentration and the $NO_2$ ratio in the ECU 220. When the NO concentration calculation unit is disposed in the ECU 220, the microcomputer 60 may calculate the NO concentration and output the calculation result to the NO concentration calculation unit in the ECU 220. In that case, the NO concentration calculation unit may calculate the $NO_2$ ratio in the ECU 220.

In the above embodiments, the deterioration degree of the oxidation catalyst (DOC) 512 is judged by the $NO_2$ ratio and the catalyst temperature. However, this should not be construed in a limiting sense. The deterioration degree of the oxidation catalyst (DOC) may be judged by a parameter different from the catalyst temperature (for example, vehicle information such as an engine drive condition) and the $NO_2$ ratio. The deterioration degree may be judged by the $NO_2$ ratio alone and without using the catalyst temperature or a different parameter.

In the embodiments, the deterioration degree of the oxidation catalyst (DOC) 512 is determined using the $NO_2$ ratio obtained from the $NO_2$ concentration/NO concentration as an evaluation value. However, this should not be construed in a limiting sense. The deterioration degree of the oxidation catalyst may be determined using the $NO_2$ ratio obtained from the $NO_X$ concentration/NO concentration as an evaluation value. The deterioration degree of the oxidation catalyst 512 may be judged using the NO concentration value.

Figure 19:
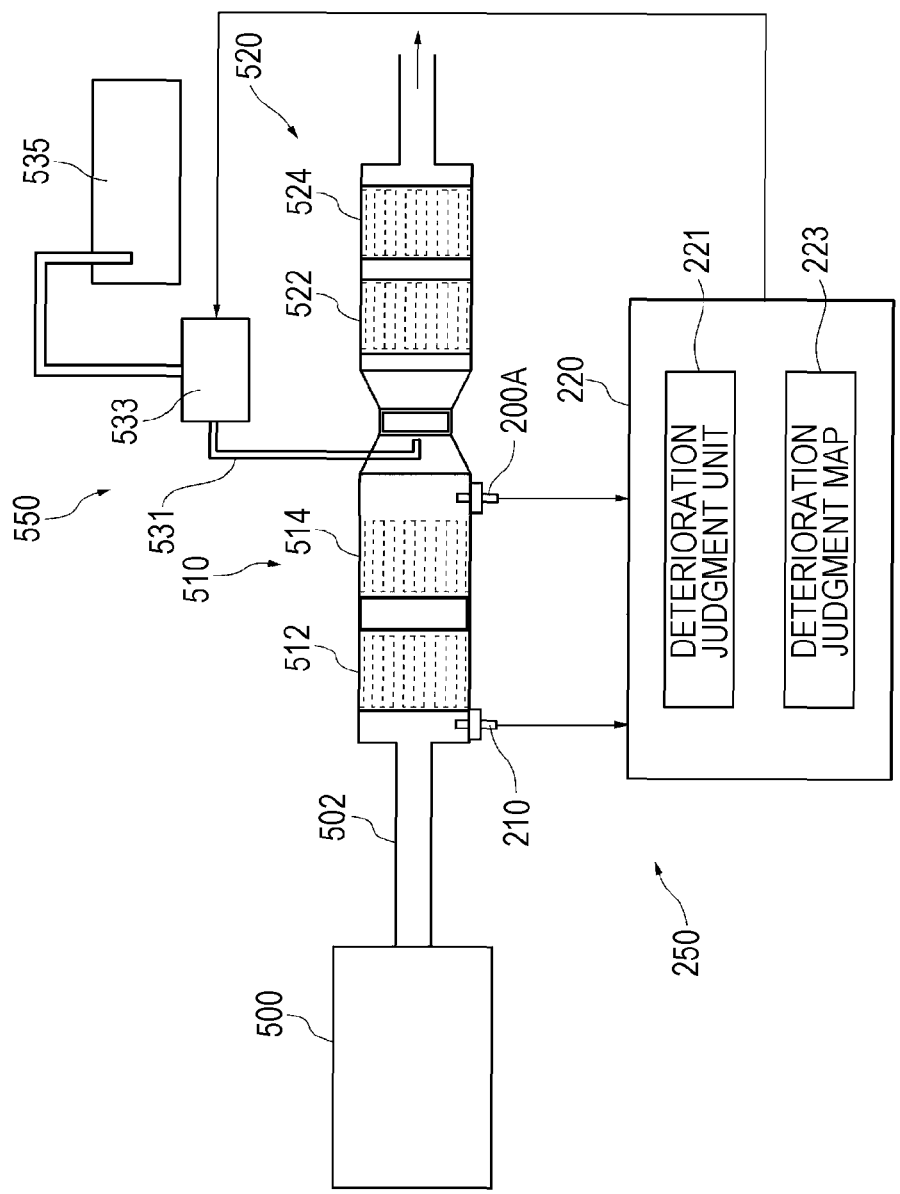
FIG. 19 is a block diagram illustrating the deterioration diagnosis device for an oxidation catalyst according to a modification of the above embodiment.

In the above embodiment, the multi-gas sensor 200A is installed at the downstream side immediately after the DOC 512 in the DPF device 510. As illustrated in FIG. 19, the multi-gas sensor 200A may be installed at the downstream side immediately after the DPF 514. Thus, disposing the multi-gas sensor 200A at the downstream side immediately after the DPF 514 inhibits PM from accumulating on the multi-gas sensor element unit 100A. This allows for reducing fluctuation of the sensor output of the multi-gas sensor element unit 100A and for diagnosing the degree of the deterioration of the DOC 512 at good accuracy.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-189824 filed Aug. 30, 2012 and Japanese Patent Application No. 2013-122621 filed Jun. 11, 2013, the above-noted applications incorporated herein by reference in their entirety.

What is claimed is:

1. A deterioration diagnosis device for determining a deterioration degree of an oxidation catalyst disposed in an exhaust passage of an internal combustion engine, the deterioration diagnosis device comprising:
 a multi-gas sensor disposed downstream of the oxidation catalyst, the multi-gas sensor including a multi-gas sensor element unit that integrally includes a $NO_2$ sensor unit and a $NO_X$ sensor unit, the $NO_2$ sensor unit directly detecting a $NO_2$ concentration in exhaust gas after passing through the oxidation catalyst, and the $NO_X$ sensor unit directly detecting a $NO_X$ concentration in the exhaust gas;
 an NO concentration calculation unit configured to calculate an NO concentration in the exhaust gas after passing through the oxidation catalyst based on the $NO_2$ concentration and the $NO_X$ concentration; and
 a deterioration judgment unit configured to determine a deterioration degree of the oxidation catalyst from an evaluation value based on the NO concentration calculated by the NO concentration calculation unit,
 wherein
 the multi-gas sensor element unit includes a plurality of $NO_2$ sensor units, and
 the respective $NO_2$ sensor units have different sensitivity ratios relative to $NO_2$.

2. The deterioration diagnosis device for oxidation catalyst as claimed in claim 1, wherein
 the multi-gas sensor element unit has a plate shape extending in an axial direction,
 the multi-gas sensor element unit includes a temperature detector for controlling a temperature of the $NO_X$ sensor unit, and
 respective ones of the plurality of $NO_2$ sensor units at least partially overlap the temperature detector in the axial direction.

* * * * *